(12) United States Patent
Ulven et al.

(10) Patent No.: US 9,499,467 B2
(45) Date of Patent: Nov. 22, 2016

(54) ORTHO-FLUORO SUBSTITUTED COMPOUNDS FOR THE TREATMENT OF METABOLIC DISEASES

(75) Inventors: Trond Ulven, Copenhagen K (DK); Elisabeth Christiansen, Odense M (DK)

(73) Assignee: CALDAN THERAPEUTICS LIMITED, Glasgow (GB)

( * ) Notice: Subject to any disclaimer, the term of this patent is extended or adjusted under 35 U.S.C. 154(b) by 0 days.

(21) Appl. No.: 14/110,531

(22) PCT Filed: Apr. 3, 2012

(86) PCT No.: PCT/DK2012/050108
§ 371 (c)(1),
(2), (4) Date: Nov. 6, 2013

(87) PCT Pub. No.: WO2012/136221
PCT Pub. Date: Oct. 11, 2012

(65) Prior Publication Data
US 2014/0058125 A1    Feb. 27, 2014

Related U.S. Application Data

(60) Provisional application No. 61/473,228, filed on Apr. 8, 2011.

(30) Foreign Application Priority Data

Apr. 8, 2011 (DK) .................................. 2011 00279

(51) Int. Cl.
| | | |
|---|---|---|
| *C07C 57/60* | (2006.01) | |
| *C07C 255/57* | (2006.01) | |
| *C07C 317/44* | (2006.01) | |
| *C07C 51/353* | (2006.01) | |
| *C07C 51/367* | (2006.01) | |
| *C07C 253/30* | (2006.01) | |
| *C07C 315/04* | (2006.01) | |
| *C07C 255/41* | (2006.01) | |
| *C07C 59/56* | (2006.01) | |

(52) U.S. Cl.
CPC .............. *C07C 57/60* (2013.01); *C07C 51/353* (2013.01); *C07C 51/367* (2013.01); *C07C 59/56* (2013.01); *C07C 253/30* (2013.01); *C07C 255/41* (2013.01); *C07C 255/57* (2013.01); *C07C 315/04* (2013.01); *C07C 317/44* (2013.01)

(58) Field of Classification Search
CPC ... C07C 57/60; C07C 315/04; C07C 51/353; C07C 51/367; C07C 253/30; C07C 59/56; C07C 317/44; C07C 255/41; C07C 355/57
See application file for complete search history.

(56) References Cited

U.S. PATENT DOCUMENTS

| | | |
|---|---|---|
| 4,160,452 A | 7/1979 | Theeuwes |
| 4,256,108 A | 3/1981 | Theeuwes |
| 4,265,874 A | 5/1981 | Bonsen et al. |
| 2004/0192743 A1 | 9/2004 | Mjalli et al. |
| 2008/0021069 A1 | 1/2008 | Itoh et al. |

FOREIGN PATENT DOCUMENTS

| | | |
|---|---|---|
| EP | 1698624 | 9/2006 |
| EP | 1731505 | 12/2006 |
| JP | 2003238403 | 8/2003 |
| WO | WO 2005/051890 | 6/2005 |
| WO | WO 2005/063729 | 7/2005 |
| WO | WO 2005/086661 | 9/2005 |
| WO | WO 2005/087710 | 9/2005 |
| WO | WO 2008/001931 | 1/2008 |
| WO | WO 2008/030618 | 3/2008 |
| WO | WO 2008/054675 | 5/2008 |
| WO | WO 2009/034388 | 3/2009 |
| WO | WO 2010/012650 | 2/2010 |
| WO | WO 2011/097300 | 8/2011 |

OTHER PUBLICATIONS

Briscoe et al., "Pharmacological regulation of insulin secretion in MIN6 cells through the fatty acid receptor GPR40: identification of agonist and antagonist small molecules", *British Journal of Pharmacology*, vol. 148, 2006, pp. 619-28.

Christiansen et al., "Discovery of Potent and Selective Agonists for the Free Fatty Acid Receptor 1 (FFA₁/GPR40), a Potential Target for the Treatment of Type II Diabetes", *J. Med. Chem.*, vol. 51, 2008, pp. 7061-7064.

Christiansen et al., "A Rapid and Efficient Sonogashira Protocol and Improved Synthesis of Free Fatty Acid 1 (FFA1) Receptor Agonists", *J. Org. Chem.*, vol. 75, 2010, pp. 1301-1304.

Christiansen et al., "Identification of a Potent and Selective Free Fatty Acid Receptor I (FFA₁/GPR40) Agonist with Favorable Physicochemical and in Vitro ADME Properties", *Journal of Medicinal Chemistry*, vol. 54, 2011, pp. 6691-6703.

Comin et al., "Conformationally Constrained Analogues of Diacylglycerol (DAG). 31. Modulation of the Biological Properties of Diacylglycerol Lactones (DAG-lactones) Containing Rigid-Rod Acyl Groups Separated from the Core Lactone by Spacer Units of Different Lengths", *J. Med. Chem.*, vol. 52, 2009, pp. 3274-3283.

Garrido et al., "Synthesis and activity of small molecule GPR40 agonists", *Bioorganic & Medicinal Chemistry Letters*, vol. 16, 2006, pp. 1840-1845.

(Continued)

*Primary Examiner* — Nyeemah A Grazier
*Assistant Examiner* — Amanda L Aguirre
(74) *Attorney, Agent, or Firm* — Merchant & Gould P.C.

(57) ABSTRACT

There is provided novel fluoro-substituted compounds capable of modulating the G-protein-coupled receptor GPR40, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

16 Claims, 2 Drawing Sheets

(56) References Cited

OTHER PUBLICATIONS

Figure 1:
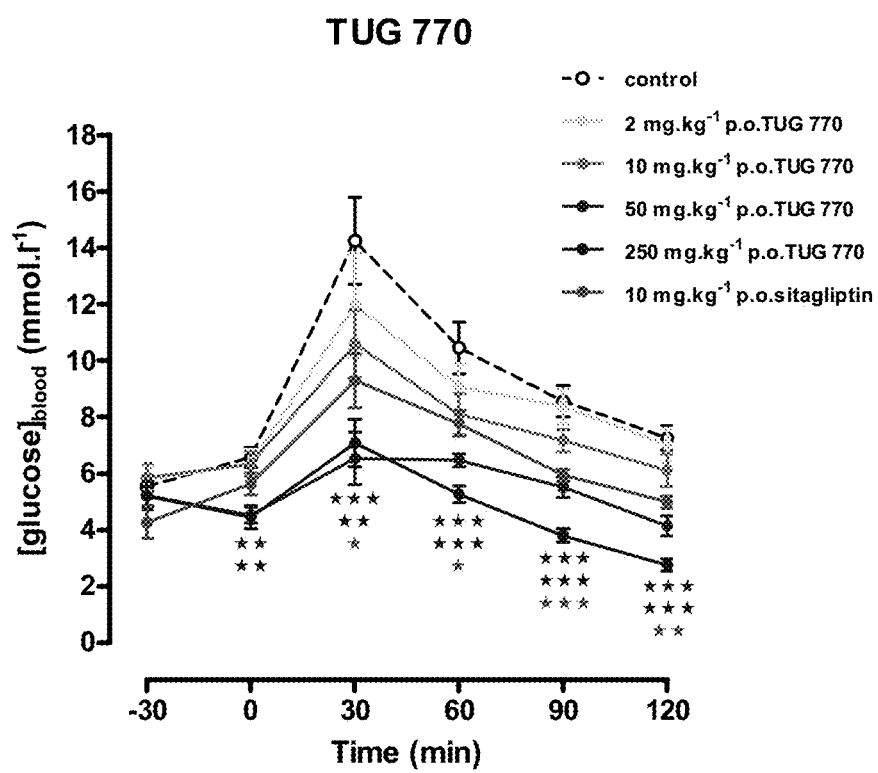

International Search Report from International Application No. PCT/DK2012/050108 mailed Jun. 29, 2012.
Tan et al., "Selective Small-Molecule Agonists of G Protein-Coupled Receptor 40 Promote Glucose-Dependent Insulin Secretion and Reduce Blood Glucose in Mice", *Diabetes*, vol. 57, 2008, pp. 2211-2219.
Winzell et al., "G-protein-coupled receptors and islet function—Implications for treatment of type 2 diabetes", *Pharmacology & Therapeutics*, vol. 116, 2007, pp. 437-448.
Sasaki et al. "Design Synthesis, and Biological Activity of Potent and Orally Available G Protein-Coupled Receptor 40 Agonists," J. Med. Chem., (2011), pp. 1365-1378.
Mikami et al., "Discovery of Phenylpropanoic Acid Derivatives Containing Polar Functionalities as Potent and Orally Bioavailable G Protein-Coupled Receptor 40 Agonists for the Treatment of Type 2 Diabetes," , J. Med. Chem., (2012), pp. 3756-3776.

ORTHO-FLUORO SUBSTITUTED COMPOUNDS FOR THE TREATMENT OF METABOLIC DISEASES

This application is a National Stage Application of PCT/DK2012/050108, filed 3 Apr. 2012, which claims benefit of Serial No. PA 2011 00279, filed 8 Apr. 2011 in Denmark, and claims benefit of U.S. Provisional Ser. No. 61/473,228, filed 8 Apr. 2011, and which applications are incorporated herein by reference. To the extent appropriate, a claim of priority is made to each of the above disclosed applications.

FIELD OF THE INVENTION

The present invention relates to novel 2-halo substituted compounds capable of modulating the G-protein-coupled receptor GPR40, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

BACKGROUND OF THE INVENTION

The production of insulin is central to the regulation of carbohydrate and lipid metabolism. Insulin imbalances lead to conditions such as type II diabetes mellitus, a serious metabolic disease that currently afflicts approximately 246 million people worldwide, and is expected to affect 380 million by 2025. Insulin is secreted from pancreatic beta-cells in response to elevated plasma glucose which is augmented by the presence of fatty acids. The recent recognition of the function of the G-protein coupled receptor GPR40 in modulating insulin secretion has provided insight into regulation of carbohydrate and lipid metabolism in vertebrates, and further provided targets for the development of therapeutic agents for disorders such as obesity, diabetes, cardiovascular disease and dyslipidemia.

GPR40 is a member of the gene superfamily of G-protein coupled receptors (GPCRs) or 7-transmembrane receptors (7TM receptors). These receptors are membrane proteins characterized as having seven transmembrane domains, and respond to a variety of molecules by activating intra-cellular signalling pathways critical to a diversity of physiological functions.

At present there is no cure for diabetes, but the disease can often be managed satisfactory, and various treatments are used to ameliorate the disease. For example, dietetic measures have been employed to balance the relative amounts of proteins, fats, and carbohydrates in a patient. Diabetes education and awareness programmes have also been implemented in several countries. In addition, diabetic conditions of moderate or severe intensity are treated by the administration of insulin. Also, prescription drugs such as thiazolinediones have been employed to rejuvenate impaired insulin production in adult onset diabetics. Other drugs are used to modulate the effectiveness of insulin. In any case, treatment of either juvenile or adult onset diabetes, has achieved only partial success. This is due to most agents targeting either improved beta-cell function or reducing insulin resistance, with the effect attenuating as the disease progressively worsens. Thus patients require the use (often daily) of a combination of agents to control the disease.

Biguanides, such as metformin, became available for treatment of type 2 diabetes in the late 1950s, and have been effective hypoglycaemic agents ever since (Vigneri and Goldfine (1987) Diabetes Care 10, 118-122). Little is known about the exact molecular mechanism of these agents. As an insulin sensitizer, metformin acts predominantly on the liver, where it suppresses glucose release (Goldfine (2001) Hospital Practice 36, 26-36). Metformin has also been shown to inhibit the enzymatic activity of complex I of the respiratory chain and thereby impairs both mitochondrial function and cell respiration, and in so doing decreasing the ATP/ADP ratio which activates AMP-activated protein kinase (AMPK), causing catabolic responses on the short term and insulin sensitization on the long term (Brunmair et al. (2004) Diabetes 53, 1052-1059; Tiikkainen et al. (2004) Diabetes 53, 2169-2176). This drug has been proven effective in both monotherapy and in combination with sulfonylureas or insulin (Davidson and Peters (1997) American Journal of Medicin 102, 99-110). Diabetes in the young is a global phenomenon that is increasing in incidence. Some key transcription factors, important for beta-cell development, differentiation and function, are implicated in diabetes in the young. Some of these are direct targets of current therapeutic agents. The cost of current diabetic drugs is very high and the development of more affordable alternative therapies would be an advantage. The global burden of type 2 diabetes is huge, and action is required to endure affordable diabetes treatment to improve the quality of life of those individuals affected.

As a result of its adipogenic effect, insulin has the undesirable effect of promoting obesity in patients with type 2 diabetes. (Moller, D. E. (2001) Nature 414:821-827). Unfortunately, other anti-diabetic drugs, including metformin, which are currently being used to stimulate glucose transport in patients with type 2 diabetes also possess adipogenic activity. Thus while current drug therapy may provide reduction in blood sugar, it often promotes obesity. Accordingly, new compositions and methods for treating hyperglycemia are desirable. Compositions that stimulate glucose uptake without generating concomitant adipogenic side effects and with no risk of causing excess insulin secretion and concequential hypoglycaemia are especially desirable.

The seven-transmembrane receptor GPR40, or free fatty acid receptor 1 (FFA$_1$/FFAR1), was recently found to be highly expressed on pancreatic beta-cells, and activated by physiological concentrations of free fatty acids. Activation of GPR40 enhanced glucose-stimulated insulin secretion (GSIS), but did not affect insulin secretion at low glucose concentrations. The enhancement of GSIS by GPR40 has been confirmed in vivo. Furthermore, two single nucleotide polymorphisms of GPR40 significantly correlating to obesity and impaired insulin secretion, further validating the link between the receptor and the disease.

WO08030618A1 (BENZO-FUSED COMPOUNDS FOR USE IN TREATING METABOLIC DISORDERS) discloses compositions for treating metabolic disorders such as type II diabetes. This document specifically relates to compounds capable of modulating GPR40.

WO05086661A2 (COMPOUNDS, PHARMACEUTICAL COMPOSITIONS AND METHODS FOR USE IN TREATING METABOLIC DISORDERS) describes alkynyl containing compounds capable of modulating the G-protein-coupled receptor GPR40, compositions comprising the compounds, and methods for their use for controlling insulin levels in viva and for the treatment of conditions such as type II diabetes.

WO08001931A2 (FUSED CYCLIC COMPOUNDS) describes novel fused cyclic compounds having a GPR40 receptor function modulating action, and which are useful as insulin secretagogues or agents for the prophylaxis or treatment of diabetes and the like.

US20080021069A1 (Receptor Function Regulating Agent) also relates to a GPR40 receptor function regulator comprising a fused imidazole compound. According to the specification the GPR40 receptor function regulator is useful as an agent for the prophylaxis or treatment of obesity, hyperinsulinemia, type 2 diabetes and the like.

WO08054675A2 (ANTIDIABETIC BICYCLIC COMPOUNDS) focuses on a new class of GPR40 agonists. The compounds are useful in the treatment of diseases that are modulated by GPR40 agonists, including type 2 diabetes and hyperglycemia that may be associated with type 2 diabetes or pre-diabetic insulin resistance.

WO05051890A1 (AMINOPHENYLCYCLOPROPYL CARBOXYLIC ACIDS AND DERIVATIVES AS AGONISTS TO GPR40) discloses novel therapeutic compounds for use as GPR40 agonists.

WO05087710A1 discloses compounds with GPR40 receptor agonistic activity. They can be a medicine which is safe and useful as a preventive/therapeutic agent for pathological states or diseases in which a GPR40 receptor participates, such as diabetes.

WO05063729A1 discloses compounds having a GPR40 receptor function modulating action, which can be used as an insulin secretagogue, an agent for the prophylaxis or treatment of diabetes and the like.

Winzell and Ahrén (G-protein-coupled receptors and islet function—Implications for treatment of type 2 diabetes—Pharmacology & Therapeutics 116 (2007) 437-448) confirm that many efforts have been made to produce small molecule GPR40 receptor agonists and antagonists to investigate their potential as drugs for type 2 diabetes. It is mentioned that in clonal β cells, insulin secretion could be potentiated by addition of a GPR40 agonist, suggesting that acute activation of GPR40 may be useful to stimulate insulin secretion. However, since the mouse model with transgenic overexpression of GPR40 exhibited impaired β-cell function and type 2 diabetes chronic activation of the receptor may cause deleterious effects. Therefore, the authors suggest that a GPR40 antagonist may be a more efficient concept because patients with type 2 diabetes usually have elevated circulating free fatty acids.

Briscoe et al (Pharmacological regulation of insulin secretion in MIN6 cells through the fatty acid receptor GPR40: identification of agonist and antagonist small molecules—British Journal of Pharmacology (2006) 148, 619-628) disclose the pharmacology of a novel small-molecule agonist of GPR40 together with a selective antagonist of GPR40. Using these compounds, the authors verify that the potentiation of insulin secretion by fatty acids appears to be mediated at least partially through GPR40, and that GPR40 agonists can function as glucose-sensitive secretagogues in vitro.

Gamido et al. (Synthesis and activity of small molecule GPR40 agonists—Bioorganic & Medicinal Chemistry Letters (2006) 16, 1840-1845) and McKeown et al (Solid phase synthesis and SAR of small molecule agonists for the GPR40 receptor—Bioorganic & Medicinal Chemistry Letters (2007) 17, 1584-1589) focus on small molecule GPR40 receptor agonists and antagonists to investigate their potential as drugs for type 2 diabetes. The data gathered in the present work suggest that a small molecule GPR40 ligand could help regulate insulin secretion and as such present GPR40 as a potential target for Type II Diabetes.

Tan et al. (Selective small-molecule agonists of G protein-coupled receptor 40 promote glucose-dependent insulin secretion and reduce blood glucose in mice—Diabetes (2008) 57, 2211-2219) studied three new selective GPR40 agonists in wild-type and GPR40 knock-out mice in acute and chronic studies, and concluded that GPR40 does not mediate the chronic toxic effect of free fatty acids on pancreatic islet function, but potentiate GSIS after both acute and chronic administration, and may therefore be of potential benefit for control of type 2 diabetes also in humans.

WO 2009/034388 (COMPOUNDS FOR THE TREATMENT OF METABOLIC DISORDERS) discloses therapeutic compounds which have dual activity as agonists of GPR119 and inhibitors of DPP-IV and are useful for the treatment of metabolic disorders including type II diabetes. In Preparation 124 on page 63 of this international application there is disclosed an intermediate, namely:

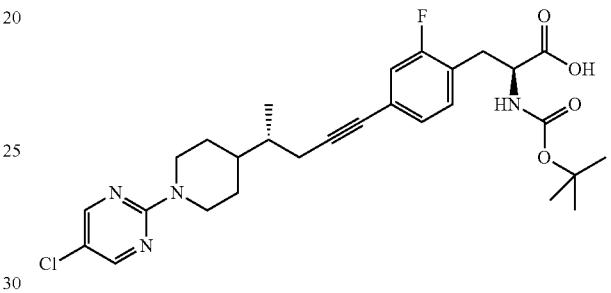

which is covered by the general formula of the present invention. Hence, this intermediate, which has not been ascribed any activity related to GPR119 and/or DPP-IV, is herewith excluded from the scope of the present invention.

Hereinafter, none of the documents disclose the compounds of the present invention.

SUMMARY OF THE INVENTION

Provided herein are compounds, pharmaceutical compositions and methods useful for treating or preventing a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema. It has surprisingly been found that ortho-fluoro substituted compounds of the relevant class possess superior antidiabetic potential compared to corresponding meta- and para-substituted analogs.

In one aspect the present invention provides a compound of the formula (I)

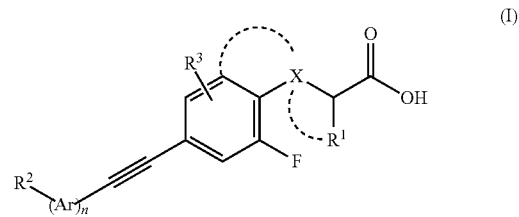

or a salt thereof
wherein
Ar is an optionally substituted monocyclic or fused aromatic or heteroaromatic ring system;
n is an integer of 0-1;
X is —$C(R^4R^5)$—, —$N(R^4)$—, —O—, or —$S(O)_m$—;
m is an integer of 0-2;
$R^1$, $R^4$, and $R^6$ are independently selected from the group consisting of hydrogen, ($C_1$-$C_{10}$)alkyl, ($C_2$-$C_{10}$)alkenyl, ($C_2$-$C_{10}$)alkynyl, ($C_1$-$C_{10}$)alkylene, ($C_1$-$C_{10}$)alkoxy, hydroxy, ($C_2$-$C_{10}$)dialkylamino, ($C_1$-$C_{10}$)alkylthio, ($C_2$-$C_{10}$)heteroalkyl, ($C_2$-$C_{10}$)heteroalkylene, ($C_3$-$C_{10}$)cycloalkyl, ($C_3$-$C_{10}$)heterocycloalkyl, ($C_3$-$C_{10}$)cycloalkylene, ($C_3$-$C_{10}$)heterocycloalkylene, halo, nitrile, ($C_1$-$C_{10}$)alkylsulfenyl, ($C_1$-$C_{10}$)alkylsulfinyl, ($C_1$-$C_{10}$)alkylsulfonyl, ($C_1$-$C_{10}$)haloalkyl, ($C_1$-$C_{10}$)perhaloalkyl, ($C_2$-$C_{10}$)-alkenyloxy, ($C_3$-$C_{10}$)-alkynyloxy, aryloxy, arylalkyloxy, heteroaryloxy, heteroarylalkyloxy, ($C_1$-$C_6$)alkyloxy-($C_1$-$C_4$)alkyl optionally substituted aryl, optionally substituted heteroaryl, and optionally substituted arylalkyl;
$R^2$ is selected from the group consisting of ($C_1$-$C_{10}$)alkyl, ($C_2$-$C_{10}$)alkenyl, ($C_2$-$C_{10}$)alkynyl, ($C_1$-$C_{10}$)alkylene, ($C_2$-$C_{10}$)heteroalkyl, ($C_2$-$C_{10}$)heteroalkenyl, ($C_2$-$C_{10}$)heteroalkylene, ($C_3$-$C_{10}$)cycloalkyl, ($C_3$-$C_{10}$)cycloalkenyl, ($C_3$-$C_{10}$)cycloalkylene, ($C_3$-$C_{10}$)heterocycloalkyl, ($C_3$-$C_{10}$)heterocycloalkenyl, ($C_3$-$C_{10}$)heterocycloalkylene, ($C_1$-$C_{10}$)haloalkyl, ($C_1$-$C_{10}$)haloalkenyl, ($C_1$-$C_{10}$)haloalkylene, ($C_1$-$C_{10}$)perhaloalkyl, ($C_1$-$C_{10}$)perhaloalkenyl, ($C_1$-$C_{10}$)perhaloalkylene, and optionally substituted arylalkyl;
Ar and $R^2$ may be further substituted by $R^6$;
$R^3$ is selected from hydrogen and halogen;
$R^5$ is selected from hydrogen and optionally substituted ($C_1$-$C_3$)alkyl;
- - - define that $R^1$ and $R^4$, when not selected from halo, may optionally be connected to the benzene ring in ortho position relative to X, to $R^3$, to X or to each other by a covalent bond, —O—, or —$S(O)_n$—.

Preferably X is —$C(R^4R^5)$—. It is also preferred that $R^1$, $R^4$ and $R^5$ are independently selected from hydrogen and ($C_1$-$C_3$)alkyl. In another preferred embodiment of the invention $R^1$ is hydrogen. Compounds, wherein $R^4$ and $R^5$ are hydrogen, are also preferred.

Concerning Ar this is preferably selected from the group consisting of an optionally substituted benzene, pyridine, thiophene, thiazole, furan, oxazole, pyrrole, pyrrazole, pyrimidine, triazole, tetrazole, naphthalene, quinoline, and indole. In a particularly preferred embodiment Ar is benzene or pyridine.

Preferably n is 1 and $R^2$ is substituted in the ortho or meta position relative to the alkyne. $R^2$ is selected from ($C_1$-$C_6$) alkyl, ($C_2$-$C_6$)alkenyl, ($C_2$-$C_6$)heteroalkyl, ($C_2$-$C_6$)heteroalkenyl, ($C_3$-$C_6$)cycloalkyl, ($C_3$-$C_6$)cycloalkenyl. In a particularly preferred embodiment $R^2$ is selected from hydrogen and ($C_1$-$C_6$)alkyl. Preferably $R^2$ is ($C_1$-$C_3$)alkyl substituted by nitrile.

In another preferred embodiment of the present invention n is 0 and $R^2$ is selected from ($C_1$-$C_{10}$)alkyl, ($C_2$-$C_{10}$)alkenyl, ($C_2$-$C_{10}$)heteroalkyl, ($C_2$-$C_{10}$)heteroalkenyl, ($C_3$-$C_{10}$)cycloalkyl, ($C_3$-$C_{10}$)cycloalkenyl, ($C_5$-$C_{10}$)bicycloalkyl, ($C_5$-$C_{10}$)heterobicycloalkyl, ($C_3$-$C_{10}$)heterocycloalkenyl. More preferably n is 0 and $R^2$ is ($C_4$-$C_6$)cycloalken-1-yl substituted by 1-3 $R^6$ groups.

Due to prior art the following compound is excluded from protection:
(S)-2-tert-Butoxycarbonylamino-3-(4-{(R)-4-[1-(5-chloro-pyrimidin-2-yl)-piperidin-4-yl]pent-1-ynyl}-2-fluorophenyl)propionic acid In some embodiments, a compound of the present invention comprise a stereomerically pure S-enantiomer. In other embodiments, the compound comprises a stereomerically pure R-enantiomer. In yet other embodiments, the compound comprises a mixture of S- and R-enantiomers.

In another aspect, the invention provides pharmaceutical compositions comprising a pharmaceutically acceptable carrier, diluent, or excipient, and a compound of any of the embodiments of the invention. According to a preferred embodiment there is provided compounds of the present invention for use as medicaments.

In another aspect, the invention provides methods for treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, hypertension, cancer, and edema. Such methods include administering to a subject in need thereof, a therapeutically effective amount of a compound of any of the embodiments. In some such embodiments, the disease or condition is type II diabetes.

In some embodiments, a compound of any of the embodiments is administered with combination with a second therapeutic agent. In some such embodiments, the second therapeutic agent is metformin or is a thiazolidinedione. The second therapeutic agent may be administered before, during, or after administration of the compound of any of the embodiments.

In another aspect, the invention provides methods for treating or preventing a disease or condition responsive to the modulation of GPR40. Such methods include administering to a subject in need thereof, a therapeutically effective amount of a compound of any of the embodiments.

In another aspect, the invention provides methods for treating or preventing a disease or condition mediated, regulated, or influenced by pancreatic beta-cells. Such methods include administering to a subject in need thereof, a therapeutically effective amount of a compound of any of the embodiments.

In another aspect, the invention provides methods for modulating GPR40 function in a cell. Such methods include contacting a cell with a compound of formula any of the embodiments.

In another aspect, the invention provides methods for modulating GPR40 function. Such methods include contacting GPR40 with a compound of any of the embodiments.

In another aspect, the invention provides methods for modulating circulating insulin concentration in a subject. Such methods include administering a compound of any of the embodiments to the subject. In some such embodiments, the circulating insulin concentration is increased in the subject after administration whereas in other such embodiments, the circulating insulin concentration is decreased in the subject after administration.

In another aspect, the invention provides the use of a compound of any of the embodiments for treating a disease or condition or for preparing a medicament for treating a disease or condition where the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes. The compounds of the invention may also be used to prepare medicaments that include a second therapeutic agent such as metformin or a thiazolidinedione.

In another aspect, the invention provides the use of a compound of any of the embodiments for modulating GPR40 or for use in the preparation of a medicament for modulating GPR40.

In another aspect, the invention provides a therapeutic composition that includes a compound of any of the embodiments and a second therapeutic agent such as those described herein, for example, metformin or a thiazolidinedione, as a combined preparation for simultaneous, separate, or sequential use in the treatment of a disease or condition mediated by GPR40. In some such embodiments, the disease or condition is type II diabetes. In some embodiments, the compound of any of the embodiments and the second therapeutic agent are provided as a single composition, whereas in other embodiments they are provided separately as parts of a kit.

DETAILED DESCRIPTION OF THE INVENTION

The terms "treat", "treating" and "treatment", as used herein, are meant to include alleviating or abrogating a condition or disease and/or its attendant symptoms. The terms "prevent", "preventing" and "prevention", as used herein, refer to a method of delaying or precluding the onset of a condition or disease and/or its attendant symptoms, barring a subject from acquiring a condition or disease, or reducing a subject's risk of acquiring a condition or disease.

The term "therapeutically effective amount" refers to that amount of the compound that will elicit the biological or medical response of a tissue, system, or subject that is being sought. The term "therapeutically effective amount" includes that amount of a compound that, when administered, is sufficient to prevent development of, or alleviate to some extent, one or more of the symptoms of the condition or disorder being treated in a subject. The therapeutically effective amount in a subject will vary depending on the compound, the disease and its severity, and the age, weight, etc., of the subject to be treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "modulate", "modulation" and the like refer to the ability of a compound to increase or decrease the function or activity of GPR40 either directly or indirectly. Inhibitors are compounds that, for example, bind to, partially or totally block stimulation, decrease, prevent, delay activation, inactivate, desensitize, or down regulate signal transduction, such as, for instance, antagonists. Activators are compounds that, for example, bind to, stimulate, increase, activate, facilitate, enhance activation, sensitize or up regulate signal transduction, such as agonists for instance. Modulation may occur in vitro or in vivo.

As used herein, the phrases "GPR40-mediated condition or disorder", "disease or condition mediated by GPR40", and the like refer to a condition or disorder characterized by inappropriate, for example, less than or greater than normal, GPR40 activity. A GPR40-mediated condition or disorder may be completely or partially mediated by inappropriate GPR40 activity.

However, a GPR40-mediated condition or disorder is one in which modulation of GPR40 results in some effect on the underlying condition or disease (e.g., a GPR40 modulator results in some improvement in patient well-being in at least some patients). Exemplary GPR40-mediated conditions and disorders include cancer and metabolic disorders, e.g., diabetes, type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, ketoacidosis, hypoglycemia, thrombotic disorders, metabolic syndrome, syndrome X and related disorders, e.g., cardiovascular disease, atherosclerosis, kidney disease, nephropathy, diabetic neuropathy, diabetic retinopathy, sexual dysfunction, dermatopathy, dyspepsia, and edema.

The term "alkyl", by itself or as part of another substituent, means, unless otherwise stated, a straight or branched chain, or cyclic hydrocarbon radical, or combination thereof, which is fully saturated, having the number of carbon atoms designated (e.g., C1-C10 means one to ten carbons). Examples of alkyl groups include methyl, ethyl, n-propyl, isopropyl, n-butyl, t-butyl, isobutyl, sec-butyl, cyclohexyl, (cyclohexyl)methyl, cyclopropyl, cyclopropylmethyl, and homologs and isomers of, for example, n-pentyl, n-hexyl, n-heptyl, n-octyl, and the like.

The term "alkenyl", by itself or as part of another substituent, means a straight or branched chain, or cyclic hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl), and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include ethynyl, 1- and 3-propynyl, 3-butynyl, and higher homologs and isomers thereof.

The term "alkylene" by itself or as part of another substituent means a divalent radical derived from alkyl, as exemplified by —$CH_2CH_2CH_2CH_2$—. The two valences may be on any carbon atom of the chain, including on the same carbon, resulting in an alkyl connected by a double bond. Typically, an alkyl (or alkylene) group will have from 1 to 24 carbon atoms, with those groups having 12 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups. The alkyl groups of a dialkylamino may be the same or different.

The term "heteroalkyl," by itself or in combination with another term, means, unless otherwise stated, a stable straight or branched chain, or cyclic hydrocarbon radical, or combinations thereof, consisting of carbon atoms and from one to three heteroatoms selected from the group consisting of O, N, and S, and wherein the nitrogen and sulfur atoms may optionally be oxidized, and the nitrogen heteroatom may optionally be quaternized. The heteroatom(s) O, N, and S may be placed at any position of the heteroalkyl group. Examples include —$CH_2CH_2OCH_3$, —$CH_2CH_2NHCH_3$, —$CH_2CH_2N(CH_3)CH_3$, —$CH_2SCH_2CH_3$, —$CH_2CH_2S(O)CH_3$, —$CH_2CH_2S(O)_2CH_3$, and —$CH_2CH=N-OCH_3$. Up to two heteroatoms may be consecutive, such as, for example, —$CH_2NH-OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group is an oxyalkyl group. For instance, ($C_2$-$C_8$)oxyalkyl is meant to include, for example —$CH_2O-CH_3$ (a $C_2$-oxyalkyl group with two carbon atoms and one oxygen replacing a carbon atom), —$CH_2CH_2CH_2CH_2OH$, and the like.

The term "heteroalkylene" by itself or as part of another substituent means a divalent radical derived from heteroalkyl, as exemplified by —$CH_2CH_2SCH_2CH_2$— and —$CH_2SCH_2$—$CH_2NHCH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied. Heteroalkylene groups such as oxymethyl groups (—$CH_2O$—) may be substituted or unsubstituted. In some embodiments, heteroalkylene groups may be substituted with an alkyl group. For example, the carbon atom of an oxymethylene group may be substituted with a methyl group in a group of formula —$CH(CH_3)O$—.

The terms "cycloalkyl" and "heterocycloalkyl" by themselves or in combination with other terms, represent, unless otherwise stated, cyclic versions of "alkyl" and "heteroalkyl" respectively. Thus, the terms "cycloalkyl" and "heterocycloalkyl" are meant to be included in the terms "alkyl" and "heteroalkyl," respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, 4,5-dihydroisoxazol-3-yl, and the like. The term "heterocycloalkyl" includes fully saturated compounds such as piperidine and compounds with partial saturation that are not aromatic. Examples of such groups include, but are not limited to, an imidazole, oxazole, or isoxazole which has been partially hydrogenated so that it only contains one double bond.

The term "cycloalkylene" and "heterocycloalkylene," by themselves or in combination with other terms, represent, unless otherwise stated, cyclic versions of "alkylene" and "heteroalkylene," respectively. Thus, the terms "cycloalkylene" and "heterocycloalkylene" are meant to be included in the terms "alkylene" and "heteroalkylene," respectively. Additionally, for heterocycloalkylene, one or more heteroatoms can occupy positions at which the heterocycle is attached to the remainder of the molecule. Typically, a cycloalkylene or heterocycloalkylene will have from 3 to 9 atoms forming the ring, more typically, 4 to 7 atoms forming the ring, and even more typically, 5 or 6 atoms will form the cycloalkylene or heterocycloalkylene ring.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2 m+1), where m is the total number of carbon atoms in the alkyl group. For example, the term "halo($C_1$-$C_4$)alkyl" is meant to include trifluoromethyl, 2,2,2-trifluoroethyl, 4-chlorobutyl, 3-bromopropyl, and the like.

Thus, the term "haloalkyl" includes monohaloalkyl (alkyl substituted with one halogen atom) and polyhaloalkyl (alkyl substituted with halogen atoms in a number ranging from two to (2 m+1) halogen atoms). The term "perhaloalkyl" means, unless otherwise stated, alkyl substituted with (2 m+1) halogen atoms, where m is the total number of carbon atoms in the alkyl group. For example, the term "perhalo (C1-C4)alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon ring. The term "heteroaryl" refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl and 4-pyridazinyl.

The term "fused aryl" means, unless otherwise stated, an aryl which is fused with another cyclic aromatic or non-aromatic ring. The term "fused heteroaryl" means, unless otherwise stated, a heteroaryl which is fused with another cyclic aromatic or non-aromatic ring. Examples of fused aryl and fused heteroaryl groups include 1-naphthyl, 2-naphthyl, 4-biphenyl, dibenzofuryl, 5-benzothiazolyl, 2-benzoxazolyl, 5-benzoxazolyl, benzooxadiazolyl, purinyl, 2-benzimidazolyl, 5-indolyl, 1H-indazolyl, carbazolyl, carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl.

Preferably, the term "aryl" refers to a phenyl group which is unsubstituted or substituted. Preferably, the term "heteroaryl" refers to a pyrrolyl, pyrazolyl, imidazolyl, pyrazinyl, oxazolyl, oxadiazolyl, isoxazolyl, thiazolyl, furyl, thienyl (thiophenyl), pyridyl, or pyrimidyl which is substituted or unsubstituted. Preferably, the term "fused aryl refers to naphthyl, indanyl, indenyl, or quinolyl. Preferably, the term "fused heteroaryl" refers to quinolyl, benzothiazolyl, purinyl, benzimidazolyl, indolyl, isoquinolyl, triazolyl, tetrazolyl, or quinoxalinyl group which is unsubstituted or substituted.

Each of the above terms (e.g., "alkyl," "heteroalkyl," "aryl" and "heteroaryl") is meant to include both substituted and unsubstituted forms of the indicated radical, unless otherwise indicated. Preferred substituents for each type of radical are provided below.

The term "substituent", which may be present on alkyl or heteroalkyl radicals, as well as those groups referred to as alkylene, alkenyl, heteroalkylene, heteroalkenyl, alkynyl, cycloalkyl, heterocycloalkyl, cycloalkenyl and heterocycloalkenyl, or on other groups indicated as "optionally substituted", can be a variety of groups selected from: —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R"', —NR'—SO$_2$NR'R"', —NR"CO$_2$R', —NH—C(NH$_2$)=NH, —NR'C(NH$_2$)=NH, —NH—C(NH$_2$)=NR', —SiR'R"R"', —S(O)R', —SO$_2$R', —SO$_2$NRR", —NR"SO$_2$R, —CN, —(C$_2$-C$_5$)alkynyl, —(C$_2$-C$_5$)alkenyl, and —NO$_2$, in a number ranging from zero to three, with those groups having zero, one or two substituents being particularly preferred. Other suitable substituents include aryl and heteroaryl groups. R', R" and R"' each independently refer to hydrogen, unsubstituted (C$_1$-C$_6$)alkyl and (C$_2$-C$_6$)heteroalkyl, unsubstituted aryl, aryl substituted with one to three halogens, unsubstituted (C$_1$-C$_4$)-alkyl, (C$_1$-C$_4$)-alkoxy or (C$_1$-C$_4$)-thioalkoxy groups, halo (C$_1$-C$_4$)alkyl, or aryl-(C$_1$-C$_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl.

Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —OC(O)R', —C(O)R', —CO$_2$R', —CONR'R", —OC(O)NR'R", —NR"C(O)R', —NR"CO$_2$R', —NR'SO$_2$NR'R"', —S(O)R', —SO$_2$R', —SO$_2$NR'R", —NR"SO$_2$R, —CN, —(C$_2$-C$_5$)alkynyl, —(C$_2$-C$_5$)alkenyl and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR'CO$_2$R', —NR'—SO$_2$NR"R"', —SO$_2$R', —SO$_2$NR'R", —NR"SO$_2$R, —CN, —(C$_2$-C$_5$)alkynyl, —(C$_2$-C$_5$)alkenyl, and —NO$_2$.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NHC(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R"' are independently selected from hydrogen, (C$_1$-C$_4$)alkyl and heteroalkyl, unsubstituted aryl and heteroaryl, (unsubstituted aryl)-(C$_1$-C$_4$)alkyl, (unsubstituted aryl)oxy-(C$_1$-C$_4$)alkyl, —C$_2$-C$_5$)alkynyl, and —(C$_2$-C$_5$)alkenyl.

As used herein, the term "benzo-fused cycloalkane ring" is meant to include bicyclic structures in which benzene is fused with a cycloalkane (or cycloheteroalkane).

As used herein, the term "heterobenzo-fused (C$_5$-C$_8$) cycloalkane ring" has the same meaning as "benzo-fused (C$_5$-C$_8$)cycloalkane ring" except the benzene of the benzo-fused (C$_5$-C$_8$)cycloalkane ring is replaced with a six-membered heteroaryl ring comprising 1 or 2 nitrogen (N) atoms. The (C$_5$-C$_8$)cycloalkane of benzo-fused (C$_5$-C$_8$)cycloalkane rings and heterobenzo-fused (C$_5$-C$_8$)cycloalkane ring may include only carbon atoms, but may also include one or more heteroatoms. Such heteroatoms typically are selected from O, N, or S.

As used herein, the term "heteroatom" is meant to include oxygen (O), nitrogen (N), and sulfur (S).

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not.

The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (EX. Eliel, Ed., Univ. of Notre Dame Press, Notre Dame, Ind., 1972).

In one aspect, a class of compounds that modulates GPR40 is described herein. Depending on the biological environment (e.g., cell type, pathological condition of the subject, etc.), these compounds can modulate, e.g., activate or inhibit, the actions of GPR40. By modulating GPR40, the compounds find use as therapeutic agents capable of regulating insulin levels in a subject.

The compounds find use as therapeutic agents for modulating diseases and conditions responsive to modulation of GPR40 and/or mediated by GPR40 and/or mediated by pancreatic beta-cells. As noted above, examples of such diseases and conditions include diabetes, obesity, hyperglycemia, glucose intolerance, insulin resistance, cancer, hyperinsulinemia, hypercholesterolemia, hypertension, hyperlipoproteinemia, hyperlipidemia, hypertriglylceridemia, dyslipidemia, ketoacidosis, hypoglycemia, metabolic syndrome, syndrome X, cardiovascular disease, atherosclerosis, kidney disease, nephropathy, thrombotic disorders, diabetic neuropathy, diabetic retinopathy, dermatopathy, dyspepsia and edema.

Additionally, the compounds are useful for the treatment and/or prevention of complications of these diseases and disorders (e.g., type II diabetes, sexual dysfunction, dyspepsia and so forth).

While the compounds of the invention are believed to exert their effects by interacting with GPR40, the mechanism of action by which the compounds act is not a limiting embodiment of the invention.

Compounds contemplated by the invention include, but are not limited to, the exemplary compounds provided herein.

In another aspect, the invention provides pharmaceutical compositions suitable for pharmaceutical use comprising one or more compounds of the invention and a pharmaceutically acceptable carrier, excipient, or diluent.

The term "composition" as used herein is intended to encompass a product comprising the specified ingredients (and in the specified amounts, if indicated), as well as any product which results, directly or indirectly, from combination of the specified ingredients in the specified amounts.

By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations.

Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol.

Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In another aspect, the invention provides methods of treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema, comprising administering to a subject in need thereof a therapeutically effective amount of a compound or composition of the invention.

In one embodiment, the disease or condition is type II diabetes.

In another aspect, the present invention provides a method for treating a disease or condition responsive to the modulation of GPR40 comprising administering to a subject in need thereof a therapeutically effective amount of a compound or composition of the invention.

In some embodiments, the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In certain embodiments, a cell to be contacted can be made to express or overexpress GPR40, for example, by expressing GPR40 from heterologous nucleic acid introduced into the cell or, as another example, by upregulating the expression of GPR40 from nucleic acid endogenous to the cell.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration.

The invention also contemplates administration of the compounds of the invention in a depot formulation, in which the active ingredient is released over a defined time period.

In the treatment or prevention of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema or other conditions or disorders associated with GPR40, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such other agents, or drugs, may be administered, by a route and in an amount commonly used therefore, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

The compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition mediated by GPR40. in some embodiments, therapeutic compositions are provided that include a compound of the invention and a second therapeutic agent as a combined preparation for simultaneous, separate or sequential use in the prophylactic treatment of a subject at risk for a disease or condition mediated by GPR40. In some such embodiments, the components are provided as a single composition. In other embodiments, the compound and the second therapeutic agent are provided separately as parts of a kit.

Examples of other therapeutic agents that may be combined with a compound of the invention, either administered separately or in the same pharmaceutical compositions, include, but are not limited to: (a) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (e.g., streptokinase, alteplase, anistreplase and reteplase), heparin, hirudin and warfarin derivatives, beta-blockers (e.g., atenolol), beta-adrenergic agonists (e.g., isoproterenol), ACE inhibitors and vasodilators (e.g., sodium nitroprusside, nicardipine hydrochloride, nitroglycerin and enaloprilat); and (c) anti-diabetic agents such as insulin and insulin mimetics, sulfonylureas (e.g., glyburide, meglinatide), biguanides, e.g., metformin (GLUCOPHAGE®), glucosidase inhibitors (acarbose), insulin sensitizers, e.g., thiazolidinone compounds, rosiglitazone (Avandia), troglitazone (Rezulin), ciglitazone, pioglitazone (ACTOS®) and englitazone, DPP-IV inhibitors, e.g., vildagliptin (Galvus®), sitagliptin (Januvia), and GLP-I analogs, e.g. exenatide (Byetta). In some embodiments, a compound of the invention may be administered along with a DPP-IV inhibitor or a GLP-I analog.

The weight ratio of the compound of the invention to the second active ingredient may be varied and will depend upon the effective dose of each ingredient. Generally, an effective dose of each will be used. Combinations of a compound of the invention and other active ingredients will generally also be within the aforementioned range, but in each case, an effective dose of each active ingredient should be used.

In another aspect, the present invention provides a method for modulating circulating insulin concentration in a subject, comprising administering a compound or composition of the invention.

EXAMPLES

General Procedure I

Sonogashira Coupling

A schlenk flask charged with $Na_2PdCl_4$ (1 mol %), 2-(di-tert-butylphosphino)-N-phenylindole (PIntB, 2 mol %), CuI (2 mol %), aryl halide (1 equiv), $H_2O$ (0.2 mL/mmol) and TMEDA (1.8 mL/mmol) was evacuated and backfilled with argon three times, then heated to 70° C. The alkyne (1.1-2 equiv) was added and the reaction heated to 80° C. After consumption of the starting material monitored by HPLC, the reaction mixture was cooled to rt, added water and extracted with EtOAc (×3). The combined extracts were washed with brine, dried over $MgSO_4$, and concentrated, and the residue was purified by flash chromatography.

General Procedure II

Ester Hydrolysis

A solution of acetylene methyl propanoate (1 equiv) in 1,4-dioxane/THF (4 mL) was added a solution of LiOH $xH_2O$ (2-3 equiv) in $H_2O$ (2 mL). The reaction was stirred at rt until complete consumption of the starting material indicated by TLC. The reaction was added water, 3% HCl until pH<1 and extracted with EtOAc (×3). The organic phases were combined, washed with brine and dried over $MgSO_4$ before concentration to the corresponding acetylene propanoic acid.

General Procedure III

Wittig Reaction

A round bottomed flask was added aryl aldehyde (1 equiv), ethyl bromoacetate (1.5 equiv), saturated aqueous $NaHCO_3$ (2 mL/mmol), EtOAc (1 mL/mmol) and $PPh_3$ (1.4 equiv) and stirred vigorously at rt. After consumption of the starting materials the reaction was added water and extracted with EtOAc (×3). The organic phases were combined, washed with brine, dried over $MgSO_4$, concentrated under vacuum and purified by flash chromatography.

General Procedure IV

Reduction $CoCl_2 6H_2O$ (0.1 equiv) and aryl acrylate (1 equiv) was dissolved in MeOH (2 mL/mmol) under argon atmosphere. $NaBH_4$ (1.25-2 equiv) was added in portions of 25-50 mg when the colour faded from black-brown to pink. After consumption of the starting materials the reaction was added water and extracted with EtOAc (×3). The organic phases were combined, washed with brine, dried over $MgSO_4$, concentrated under vacuum and purified by flash chromatography.

Intermediate 1

(E)-Ethyl 3-(4-bromo-2-fluorophenyl)acrylate

A round bottomed flask was added 4-bromo-2-fluorobenzaldehyde (1005 mg, 4.93 mmol), ethyl 2-bromoacetate (0.80 mL, 7.21 mmol), aqueous $NaHCO_3$ and $PPh_3$ (1.81 g, 6.90 mmol) and stirred vigorously at rt. After consumption of the starting materials the reaction was added water and extracted with EtOAc (×3). The organic phases were combined, washed with brine, dried over $MgSO_4$, concentrated under vacuum and purified by flash chromatography ($SiO_2$, EtOAc:petroleum ether, 1:5) to give 1178 mg (87%) of a clear oil (white solid at 5° C.): $R_t$=13.67 min (HPLC); $^1H$ NMR ($CDCl_3$) δ 7.72 (d, J=16.2 Hz, 1H), 7.40 (t, J=8.1 Hz, 1H), 7.34-7.27 (m, 2H), 6.52 (d, J=16.2 Hz, 1H), 4.27 (q, J=7.1 Hz, 2H), 1.34 (t, J=7.1 Hz, 3H); $^{13}C$ NMR ($CDCl_3$) δ 166.6, 160.9 (d, J=258.3 Hz), 136.0 (d, J=2.4 Hz), 129.9 (d, J=3.7 Hz), 128.0 (d, J=3.7 Hz), 124.4 (d, J=9.9 Hz), 121.7 (d, J=11.8 Hz), 121.5 (d, J=6.7 Hz), 119.9 (d, J=25.1 Hz), 60.8, 14.3.

Intermediate 2

Ethyl 3-(4-bromo-2-fluorophenyl)propanoate

The title compound was prepared from (E)-ethyl 3-(4-bromo-2-fluorophenyl)acrylate (1124 mg, 4.12 mmol) and $NaBH_4$ (277 mg, 7.33 mmol) at 0° C. according to the general procedure IV to give 979 mg (86%) of a clear oil after purification by flash chromatography ($SiO_2$, EtOAc: petroleum ether, 1:5): $R_t$=13.24 min (HPLC); $^1H$ NMR ($CDCl_3$) δ 7.22-7.17 (m, 2H), 7.10 (t, J=8.1 Hz, 1H), 4.12 (q, J=7.1 Hz, 2H), 2.93 (t, J=7.6 Hz, 2H), 2.60 (t, J=7.6 Hz, 2H), 1.23 (t, J=7.1 Hz, 3H); $^{13}C$ NMR ($CDCl_3$) δ 172.4, 161.0 (d, J=251.5 Hz), 131.8 (d, J=5.1 Hz), 127.3 (d, J=3.0 Hz), 126.6 (d, J=16.2 Hz), 120.2 (d, J=9.1 Hz), 119.0 (d, J=25.3 Hz), 60.6, 34.1 (d, J=1.0 Hz), 24.2 (d, J=2.0 Hz), 14.2; ESI-MS m/z 297.0 (M+Na$^+$).

Example 1

3-(2-Fluoro-4-(phenylethynyl)phenyl)propanoic acid

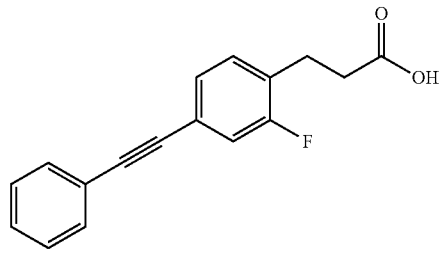 [SMILES: O=C(O)CCc1ccc(C#Cc2ccccc2)cc1F]

Ethyl 3-(2-fluoro-4-(phenylethynyl)phenyl)propanoate was prepared from ethyl 3-(4-bromo-2-fluorophenyl)propanoate (139 mg, 0.51 mmol) and phenylacetylene (0.07 mL, 0.64 mmol) according to the general procedure I to give 104 mg (69%) of an orange oily product after purification by flash chromatography ($SiO_2$, EtOAc:petroleum ether, 1:5):

$R_f$=0.47 (EtOAc:petroleum ether, 1:2); $^1$H NMR (CDCl$_3$) δ 7.56-7.48 (m, 2H), 7.39-7.31 (m, 3H), 7.25-7.15 (m, 3H), 4.13 (q, J=7.1 Hz, 2H), 2.98 (t, J=7.6 Hz, 2H), 2.63 (t, J=7.7 Hz, 2H), 1.23 (t, J=7.1 Hz, 3H); $^{13}$C NMR (CDCl$_3$) δ 172.5, 160.7 (d, J=246.4 Hz), 131.7, 130.6 (d, J=6.1 Hz), 128.5, 128.4, 128.1 (d, J=15.1 Hz), 127.5 (d, J=3.0 Hz), 123.2 (d, J=10.1 Hz), 122.9, 118.3 (d, J=24.2 Hz), 89.9, 88.1 (d, J=4.0 Hz), 60.6, 34.2, 24.6 (d, J=2.0 Hz), 14.2; ESI-MS m/z 319.1 (M+Na$^+$).

The title compound was prepared from ethyl 3-(2-fluoro-4-(phenylethynyl)phenyl)propanoate (84 mg, 0.28 mmol) according to the general procedure II to give 63 mg (79%) of a pale yellow solid (purity 99.7% by HPLC) after purification by flash chromatography (SiO$_2$, EtOAc:petroleum ether, 1:2): $R_t$=12.49 min (HPLC); $^1$H NMR (DMSO-d$_6$) δ 12.24 (s, 1H), 7.59-7.53 (m, 2H), 7.49-7.41 (m, 3H), 7.40-7.30 (m, 3H), 2.87 (t, J=7.6 Hz, 2H), 2.56 (t, J=7.6 Hz, 2H); $^{13}$C NMR (DMSO-d$_6$) δ 173.3, 160.0 (d, J=245.4 Hz), 131.3, 130.9 (d, J=5.1 Hz), 128.9, 128.7, 128.6, 127.5 (d, J=3.0 Hz), 121.9, 121.8 (d, J=10.1 Hz), 117.7 (d, J=24.2 Hz), 89.7, 88.0 (d, J=3.0 Hz), 33.3, 23.5; ESI-HRMS calcd for C$_{17}$H$_{13}$FO$_2$Na (M+Na$^+$) 291.0793. found 291.0806.

Example 2

3-(2-Fluoro-4-(3-methylbut-3-en-1-yn-1-yl)phenyl)propanoic acid

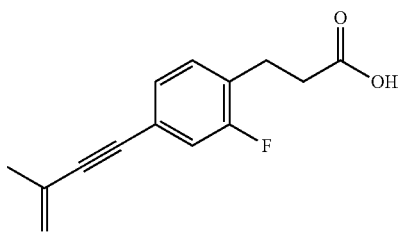 [SMILES: C=C(C)C#Cc1ccc(CCC(=O)O)c(F)c1]

Ethyl 3-(2-fluoro-4-(3-methylbut-3-en-1-yn-1-yl)phenyl)propanoate was prepared from ethyl 3-(4-bromo-2-fluorophenyl)propanoate (127 mg, 0.50 mmol) and 2-methylbut-1-en-3-yne (60 μL, 0.63 mmol) according to the general procedure I to give 100 mg (77%) of a yellow oily product after purification by flash chromatography (SiO$_2$, EtOAc:petroleum ether, 1:9): $R_f$=0.52 (EtOAc:petroleum ether, 1:2); $^1$H NMR (CDCl$_3$) δ 7.26-6.97 (m, 3H), 5.35 (d, J=33.2 Hz, 2H), 4.12 (q, J=7.1 Hz, 2H), 3.00-2.86 (m, 2H), 2.67-2.57 (m, 2H), 1.97 (s, 3H), 1.23 (t, J=7.1 Hz, 3H); $^{13}$C NMR (CDCl$_3$) δ 172.5, 160.6 (d, J=247.0 Hz), 130.5 (d, J=6.1 Hz), 127.9 (d, J=16.2 Hz), 127.5 (d, J=3.3 Hz), 126.6, 123.1 (d, J=9.1 Hz), 122.4, 118.2 (d, J=24.2 Hz), 91.1, 87.1 (d, J=3.2 Hz), 60.5, 34.2 (d, J=1.2 Hz), 24.6 (d, J=2.3 Hz), 23.4, 14.2.

The title compound was prepared from ethyl 3-(2-fluoro-4-(3-methylbut-3-en-1-yn-1-yl)phenyl)propanoate (79 mg, 0.30 mmol) according to the general procedure II to give 65 mg (92%) of a pale yellow solid (purity 97.5% by HPLC): $R_t$=12.03 min (HPLC); $^1$H NMR (CDCl$_3$) δ 11.24 (s, 1H), 7.28-6.98 (m, 3H), 5.35 (d, J=33.7 Hz, 2H), 2.97 (t, J=7.5 Hz, 2H), 2.68 (t, J=6.9 Hz, 2H), 1.97 (s, 3H); $^{13}$C NMR (CDCl$_3$) δ 178.6, 160.6 (d, J=247.1 Hz), 130.5 (d, J=6.1 Hz), 127.5 (d, J=3.0 Hz), 127.5 (d, J=16.1 Hz), 126.6, 123.4 (d, J=10.1 Hz), 122.5, 118.3 (d, J=24.2 Hz), 91.1, 87.0 (d, J=3.0 Hz), 33.9, 24.2 (d, J=2.0 Hz), 23.4; ESI-HRMS calcd for C$_{14}$H$_{15}$FO$_2$ (M+H$^+$) 233.0972. found 233.0963.

Intermediate 3

Methyl 3-(4-ethynyl-2-fluorophenyl)propanoate

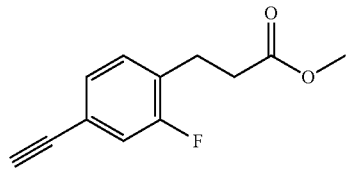

Ethyl 3-(2-fluoro-4-((trimethylsilyl)ethynyl)phenyl)propanoate was prepared from ethyl 3-(4-bromo-2-fluorophenyl)propanoate (670 mg, 2.44 mmol) and trimethylsilylacetylene (0.64 mL, 4.93 mmol) according to the general procedure I. The crude product was dissolved in MeOH (25 mL), added potassium carbonate (683 mg, 4.94 mmol) and stirred vigorously for 3 hours at room temperature. The reaction was added water and extracted with EtOAc. The organic phases were combined, washed with brine, dried over MgSO$_4$, concentrated under vacuum and purified by flash chromatography (SiO$_2$, EtOAc:petroleum ether, 1:5) to give 375 mg (74%) of a yellow oil: $R_f$: 0.49 (EtOAc:petroleum ether, 1:2): $^1$H NMR (CDCl$_3$) δ 7.24-7.10 (m, 3H), 3.67 (s, 3H), 3.07 (s, 1H), 2.97 (t, J=7.7 Hz, 2H), 2.63 (t, J=7.7 Hz, 2H); $^{13}$C NMR (CDCl$_3$) δ 172.9, 160.5 (d, J=247.5 Hz), 130.7 (d, J=6.1 Hz), 128.7 (d, J=16.2 Hz), 128.1 (d, J=4.0 Hz), 122.0 (d, J=9.1 Hz), 118.9 (d, J=24.2 Hz), 82.3 (d, J=3.0 Hz), 77.8, 51.7, 33.9 (d, J=1 Hz), 24.5 (d, J=3.0 Hz); ESI-MS m/z 229.1 (M+Na$^+$).

Example 3

(Z)-3-(2-Fluoro-4-(3-methylpent-3-en-1-yn-1-yl)phenyl)propanoic acid

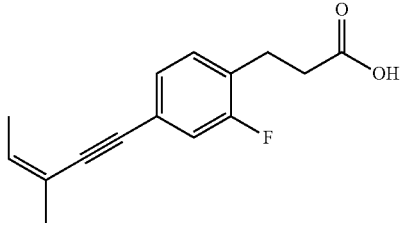 [SMILES: C/C=C(/C)C#Cc1ccc(CCC(=O)O)c(F)c1]

Methyl (Z)-3-(2-fluoro-4-(3-methylpent-3-en-1-yn-1-yl)phenyl)propanoate was prepared from methyl 3-(4-ethynyl-2-fluorophenyl)propanoate (105 mg, 0.51 mmol) and (Z)-2-bromobut-2-ene (60 μL, 0.59 mmol) according to the general procedure I to give 60 mg (45%) of a pale yellow oily product after purification by flash chromatography (SiO$_2$, EtOAc:petroleum ether, 1:6): $R_f$=0.62 (EtOAc:petroleum ether, 1:2); $^1$H NMR (CDCl$_3$) δ 7.18-7.06 (m, 3H), 5.86-5.76 (m, 1H), 3.67 (s, 3H), 2.97 (t, J=7.6 Hz, 2H), 2.63 (t, J=7.7 Hz, 2H), 1.96-1.90 (m, 3H), 1.90-1.84 (m, 3H); $^{13}$C NMR (CDCl$_3$) δ 173.0, 160.6 (d, J=246.9 Hz), 131.3, 130.5 (d, J=5.7 Hz), 127.5 (d, J=16.1 Hz), 127.3 (d, J=3.2 Hz), 123.7 (d, J=9.9 Hz), 118.5, 118.1 (d, J=23.6 Hz), 91.9 (d, J=3.1 Hz), 89.3, 51.7, 34.0 (d, J=1.3 Hz), 24.6 (d, J=2.3 Hz), 22.8, 16.3; ESI-MS m/z 261.1 (M+H±).

The title compound was prepared from methyl (Z)-3-(2-fluoro-4-(3-methylpent-3-en-1-yn-1-yl)phenyl)propanoate (54 mg, 0.21 mmol) according to the general procedure II to give 44 mg (86%) of a pale yellow solid (purity 99.5% by HPLC): $R_f$=12.56 min (HPLC); $^1$H NMR (CDCl$_3$) δ 7.18-7.08 (m, 3H), 5.86-5.77 (m, 1H), 2.97 (t, J=7.6 Hz, 2H), 2.68 (t, J=7.7 Hz, 2H), 1.93-1.90 (m, 3H), 1.90-1.84 (m, 3H); $^{13}$C NMR (CDCl$_3$) δ 178.4, 160.6 (d, J=247.0 Hz), 133.4, 130.5 (d, J=5.8 Hz), 127.4 (d, J=3.2 Hz), 127.2 (d, J=16.1 Hz), 123.8 (d, J=9.8 Hz), 118.5, 118.2 (d, J=23.5 Hz), 91.8 (d, J=3.3 Hz), 89.4, 33.9, 24.2 (d, J=2.3 Hz), 22.8, 16.4; ESI-HRMS calcd for C$_{15}$H$_{15}$FO$_2$Na (M+Na$^+$) 269.0948. found 269.0955.

Example 4

(E)-3-(2-Fluoro-4-(3-methylpent-3-en-1-yn-1-yl)phenyl)propanoic acid

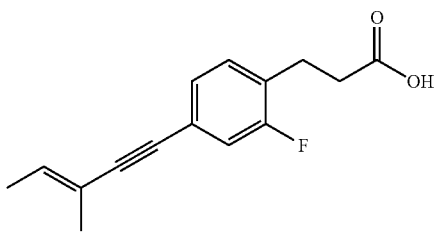 [SMILES: C/C=C(\C)C#Cc1ccc(CCC(=O)O)c(F)c1]

Methyl (E)-3-(2-fluoro-4-(3-methylpent-3-en-1-yn-1-yl)phenyl)propanoate was prepared from methyl 3-(4-ethynyl-2-fluorophenyl)propanoate (105 mg, 0.51 mmol) and (E)-2-bromobut-2-ene (60 μL, 0.59 mmol) according to the general procedure I to give 85 mg (64%) of a pale yellow oily product after purification by flash chromatography (SiO$_2$, EtOAc:petroleum ether, 1:6): $R_f$=0.62 (EtOAc:petroleum ether, 1:2); $^1$H NMR (CDCl$_3$) δ 7.16-7.10 (m, 2H), 7.07 (d, J=10.9 Hz, 1H), 6.08-5.98 (m, 1H), 3.66 (s, 3H), 2.95 (t, J=7.7 Hz, 2H), 2.62 (t, J=7.7 Hz, 2H), 1.86 (s, 3H), 1.74 (d, J=7.1 Hz, 3H); $^{13}$C NMR (CDCl$_3$) δ 173.0, 160.6 (d, J=246.4 Hz), 133.4, 130.4 (d, J=5.7 Hz), 127.3 (d, J=16.1 Hz), 127.3 (d, J=3.2 Hz), 123.8 (d, J=9.8 Hz), 118.3, 118.1 (d, J=23.6 Hz), 93.1, 84.5 (d, J=3.2 Hz), 51.7, 34.0 (d, J=1.3 Hz), 24.5 (d, J=2.4 Hz), 16.8, 14.2.

The title compound was prepared from methyl (E)-3-(2-fluoro-4-(3-methylpent-3-en-1-yn-1-yl)phenyl)propanoate (78 mg, 0.30 mmol) according to the general procedure II to give 68 mg (92%) of a white solid (purity 99.4% by HPLC): $R_f$=12.53 min (HPLC); $^1$H NMR (CDCl$_3$) δ 7.17-7.10 (m, 2H), 7.07 (d, J=11.1 Hz, 1H), 6.08-5.99 (m, 1H), 2.96 (t, J=7.7 Hz, 2H), 2.67 (t, J=7.7 Hz, 2H), 1.86 (s, 3H), 1.74 (dd, J=7.1, 0.7 Hz, 3H); $^{13}$C NMR (CDCl$_3$) δ 178.5, 160.6 (d, J=246.9 Hz), 133.5, 130.4 (d, J=5.6 Hz), 127.4 (d, J=3.2 Hz), 126.9 (d, J=16.1 Hz), 123.9 (d, J=9.8 Hz), 118.3, 118.1 (d, J=23.6), 93.2, 84.5 (d, J=3.1 Hz), 33.9 (d, J=1.0 Hz), 24.2 (d, J=2.4 Hz), 16.8, 14.2; ESI-HRMS calcd for C$_{15}$H$_{15}$FO$_2$Na (M+Na$^+$) 269.0948. found 269.0961.

Example 5

3-(2-Fluoro-4-(o-tolylethynyl)phenyl)propanoic acid

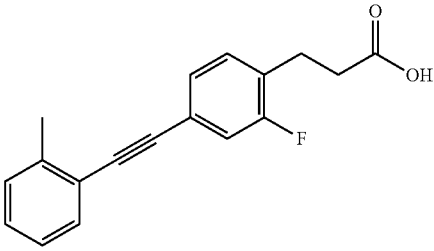 [SMILES: Cc1ccccc1C#Cc1ccc(CCC(=O)O)c(F)c1]

Methyl 3-(2-fluoro-4-(o-tolylethynyl)phenyl)propanoate was prepared from methyl 3-(4-ethynyl-2-fluorophenyl)propanoate (110 mg, 0.53 mmol) and 1-bromo-2-methylbenzene (70 μL, 0.58 mmol) according to the general procedure I to give 82 mg (52%) of a pale yellow oily product after purification by flash chromatography (SiO$_2$, EtOAc:petroleum ether, 1:8): $R_f$=0.35 (EtOAc:petroleum ether, 1:2); $^1$H NMR (CDCl$_3$) δ 7.47 (d, J=7.5 Hz, 1H), 7.28-7.12 (m, 6H), 3.67 (s, 3H), 2.98 (t, J=7.6 Hz, 2H), 2.64 (t, J=7.6 Hz, 2H), 2.49 (s, 3H); $^{13}$C NMR (CDCl$_3$) δ 172.9, 160.7 (d, J=247.1 Hz), 140.3, 131.9, 130.6 (d, J=6.1 Hz), 129.5, 128.6, 127.9 (d, J=16.2 Hz), 127.4 (d, J=3.0 Hz), 125.6, 123.5 (d, J=10.1 Hz), 122.7, 118.2 (d, J=23.2 Hz), 92.1 (d, J=3.1 Hz), 88.9, 51.7, 34.0 (d, J=1.2 Hz), 24.6 (d, J=2.3 Hz), 20.7; ESI-MS m/z 297.1 (M+H$^+$).

The title compound was prepared from methyl 3-(2-fluoro-4-(o-tolylethynyl)phenyl)propanoate (72 mg, 0.24 mmol) according to the general procedure II to give 65 mg (95%) of a white solid (purity 99.8% by HPLC): $R_f$=13.03 min (HPLC); $^1$H NMR (CDCl$_3$) δ 7.48 (d, J=7.5 Hz, 1H), 7.28-7.12 (m, 6H), 3.00 (t, J=7.5 Hz, 2H), 2.70 (t, J=7.6 Hz, 2H), 2.50 (s, 3H); $^{13}$C NMR (CDCl$_3$) δ 178.5, 160.7 (d, J=247.3 Hz), 140.3, 131.9, 130.6 (d, J=6.1 Hz), 129.5, 128.6, 127.5 (d, J=16.1 Hz), 127.5 (d, J=3.2 Hz), 125.6, 123.6 (d, J=10.1 Hz), 122.6, 118.2 (d, J=24.2 Hz), 92.0 (d, J=3.2 Hz), 89.0, 33.9, 24.3 (d, J=2.1 Hz), 20.7; ESI-HRMS calcd for C$_{18}$H$_{16}$FO$_2$ (M+H$^+$) 283.1129. found 283.1139.

Example 6

3-(4-((2-(Cyanomethyl)phenyl)ethynyl)-2-fluorophenyl)propanoic acid

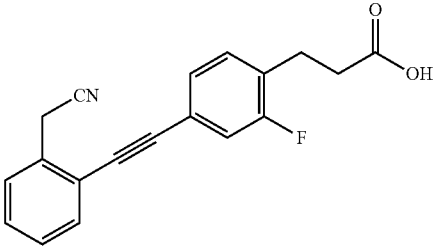 [SMILES: N#CCc1ccccc1C#Cc1ccc(CCC(=O)O)c(F)c1]

Methyl 3-(4-((2-(cyanomethyl)phenyl)ethynyl)-2-fluorophenyl)propanoate was prepared from methyl 3-(4-ethynyl-2-fluorophenyl)propanoate (105 mg, 0.51 mmol) and 2-(2-iodophenyl)acetonitrile (149 mg, 0.61 mmol) according to the general procedure I to give 105 mg (64%) of pale yellow solid after purification by flash chromatography (SiO$_2$, EtOAc:petroleum ether, 1:5): R$_f$=0.29 (EtOAc:petroleum ether, 1:2); $^1$H NMR (CDCl$_3$) δ 7.53 (dd, J=24.1 Hz, 7.4 Hz, 2H), 7.43-7.31 (m, 2H), 7.30-7.17 (m, 3H), 3.95 (s, 2H), 3.68 (s, 3H), 3.00 (t, J=7.6 Hz, 2H), 2.65 (t, J=7.6 Hz, 2H); $^{13}$C NMR (CDCl$_3$) δ 172.9, 160.7 (d, J=248.5 Hz), 132.5, 131.8, 130.9 (d, J=5.1 Hz), 129.3, 128.7 (d, J=16.2 Hz), 128.3, 128.3, 127.6 (d, J=3.0 Hz), 122.5, 122.4 (d, J=9.1 Hz), 118.3 (d, J=24.2 Hz), 117.3, 94.4 (d, J=3.3 Hz), 86.5, 51.7, 33.9 (d, J=1.0 Hz), 24.6 (d, J=2.2 Hz), 22.8; ESI-MS m/z 344.1 (M+Na$^+$).

The title compound was prepared from methyl 3-(4-((2-(cyanomethyl)phenyl)ethynyl)-2-fluorophenyl)propanoate (73 mg, 0.23 mmol) according to the general procedure II to give 48 mg (69%) of a white solid (purity 98.7% by HPLC) after purification by flash chromatography (SiO$_2$, EtOAc [with 1% AcOH]:petroleum ether, 2:3): R$_t$=11.65 min (HPLC); $^1$H NMR (Acetone-d$_6$) δ 7.60 (dd, J=17.5 Hz, 7.5 Hz, 2H), 7.53-7.33 (m, 5H), 4.16 (s, 2H), 2.99 (t, J=7.6 Hz, 2H), 2.67 (t, J=7.6 Hz, 2H); $^{13}$C NMR (Acetone-d$_6$) δ 173.5, 161.5 (d, J=245.8 Hz), 134.1, 133.2, 132.0 (d, J=6.1 Hz), 130.4, 130.1 (d, J=15.2 Hz), 129.6, 129.1, 128.5 (d, J=3.0 Hz), 123.3 (d, J=9.9 Hz), 123.3, 118.8 (d, J=24.3 Hz), 118.4, 94.8 (d, J=3.0 Hz), 87.4, 34.0, 24.8 (d, J=2.5 Hz), 22.9; ESI-HRMS calcd for C$_{19}$H$_{14}$FNO$_2$Na (M+Na$^+$) 330.0901. found 330.0907.

Example 7

3-(4-((5-Cyano-2-methylphenyl)ethynyl)-2-fluorophenyl)propanoic acid

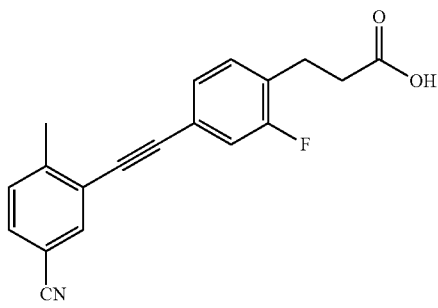 [SMILES: Cc1ccc(C#N)cc1C#Cc1ccc(CCC(=O)O)c(F)c1]

Methyl 3-(4-((5-cyano-2-methylphenyl)ethynyl)-2-fluorophenyl)propanoate was prepared from methyl 3-(4-ethynyl-2-fluorophenyl)propanoate (110 mg, 0.53 mmol) and 3-iodo-4-methylbenzonitrile (140 mg, 0.58 mmol) according to the general procedure I to give 115 mg (68%) of pale yellow oily product after purification by flash chromatography (SiO$_2$, EtOAc:petroleum ether, 1:5): R$_f$=0.21 (EtOAc:petroleum ether, 1:2); $^1$H NMR (CDCl$_3$) δ 7.75 (s, 1H), 7.50 (d, J=7.9 Hz, 1H), 7.34 (d, J=7.9 Hz, 1H), 7.25-7.17 (m, 3H), 3.68 (s, 3H), 3.00 (t, J=7.6 Hz, 2H), 2.65 (t, J=7.6 Hz, 2H), 2.56 (s, 3H); $^{13}$C NMR (CDCl$_3$) δ 172.8, 160.7 (d, J=247.7 Hz), 145.6, 135.2, 131.5, 130.8 (d, J=5.7 Hz), 130.4, 128.8 (d, J=16.2 Hz), 127.6 (d, J=4.0 Hz), 124.3, 122.4 (d, J=9.1 Hz), 118.3 (d, J=24.0 Hz), 118.3, 110.1, 94.2 (d, J=3.1 Hz), 86.4, 51.7, 33.9 (d, J=1.1 Hz), 24.6 (d, J=2.3 Hz), 21.2; ESI-MS m/z 344.1 (M+Na$^+$).

The title compound was prepared from methyl 3-(4-((5-cyano-2-methylphenyl)ethynyl)-2-fluorophenyl)propanoate (110 mg, 0.34 mmol) according to the general procedure II to give 71 mg (68%) of a white solid (purity 99.3% by HPLC) after purification by flash chromatography (SiO$_2$, EtOAc[with 1% AcOH]:petroleum ether, 2:3): R$_t$=12.26 min (HPLC); $^1$H NMR (Acetone-d$_6$) δ 7.88 (s, 1H), 7.69 (d, J=7.9 Hz, 1H), 7.54 (d, J=8.0 Hz, 1H), 7.47-7.29 (m, 3H), 2.99 (t, J=7.6 Hz, 2H), 2.66 (dd, J=14.8 Hz, 7.2 Hz, 2H), 2.59 (s, 3H); $^{13}$C NMR (Acetone-d$_6$) δ 173.5, 161.6 (d, J=245.4 Hz), 146.6, 135.8, 132.7, 132.1 (d, J=5.7 Hz), 131.7, 130.3 (d, J=15.9 Hz), 128.5 (d, J=3.3 Hz), 125.0, 123.1 (d, J=9.8 Hz), 118.9, 118.7, 111.0, 94.8 (d, J=3.1 Hz), 87.1, 34.0, 24.8, (d, J=2.6 Hz), 21.1; ESI-HRMS calcd for C$_{19}$H$_{14}$FNO$_2$Na (M+Na$^+$) 330.0901. found 330.0892.

Intermediate 4

1-Bromo-2-((methylsulfonyl)methyl)benzene

2-Bromobenzylbromide (250 mg, 1.00 mmol), sodium methanesulfinate (303 mg, 2.97 mmol) and DMF (2.5 mL) was added to a 10 mL cone shaped flask and stirred at 60° C. for 1 hour. The reaction was cooled to room temperature, added water and extracted with EtOAc (×3). The organic phases were combined, washed with water (×2), brine (×1), dried over MgSO$_4$ and concentrated under vacuum to give 235 mg (94%) of a white solid: R$_f$=0.34 (EtOAc:petroleum ether, 1:2); $^1$H NMR (CDCl$_3$) δ 7.67-7.63 (m, 1H), 7.61 (dd, J=7.7 Hz, 1.5 Hz, 1H), 7.40 (td, J=7.6 Hz, 0.9 Hz, 1H), 7.27 (td, J=7.8 Hz, 1.6 Hz, 1H), 4.52 (s, 2H), 2.82 (s, 3H); $^{13}$C NMR (CDCl$_3$) δ 133.4, 133.1, 130.8, 128.5, 128.3, 125.0, 60.4, 39.9; ESI-MS m/z 270.9 (M+Na$^+$).

Example 8

3-(2-Fluoro-4-((2-((methylsulfonyl)methyl)phenyl)ethynyl)phenyl)propanoic acid

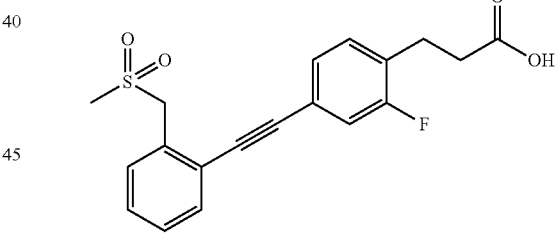

Methyl 3-(2-fluoro-4-((2-((methylsulfonyl)methyl)phenyl)ethynyl)phenyl)propanoate was prepared from methyl 3-(4-ethynyl-2-fluorophenyl)propanoate (104 mg, 0.50 mmol) and 1-bromo-2-((methylsulfonyl)methyl)benzene (136 mg, 0.54 mmol) according to the general procedure I to give 136 mg (72%) of a pale yellow solid after purification by flash chromatography (SiO$_2$, EtOAc:petroleum ether, 1:2): R$_f$=0.12 (EtOAc:petroleum ether, 1:2); $^1$H NMR (CDCl$_3$) δ 7.67-7.57 (m, 2H), 7.47-7.37 (m, 2H), 7.30-7.16 (m, 3H), 4.57 (s, 2H), 3.69 (s, 3H), 3.01 (t, J=7.6 Hz, 2H), 2.80 (s, 3H), 2.66 (t, J=7.6 Hz, 2H); $^{13}$C NMR (CDCl$_3$) δ 172.8, 160.7 (d, J=248.1 Hz), 133.3 (d, J=32.7 Hz), 132.8, 131.5, 131.0 (d, J=5.7 Hz), 130.3, 129.5, 129.2, 127.5 (d, J=3.3 Hz), 123.6, 122.0 (d, J=9.7 Hz), 118.3 (d, J=24.0 Hz), 93.4 (d, J=3.2 Hz), 87.2, 59.5, 51.9, 39.4, 33.9 (d, J=1.2 Hz), 24.6 (d, J=2.3 Hz); ESI-MS m/z 375.1 (M+H±).

The title compound was prepared from methyl 3-(2-fluoro-4-((2-((methylsulfonyl)-methyl)phenyl)ethynyl)phenyl)propanoate (109 mg, 0.29 mmol) according to the general procedure II to give 100 mg (95%) of a pale yellow solid (purity 99.6% by HPLC): $R_t$=10.71 min (HPLC); $^1$H NMR (Acetone-$d_6$) δ 7.73-7.59 (m, 2H), 7.51-7.31 (m, 5H), 4.70 (s, 2H), 2.99 (t, J=7.6 Hz, 2H), 2.93 (s, 3H), 2.67 (t, J=7.6 Hz, 2H); $^{13}$C NMR (Acetone-$d_6$) δ 173.5, 161.5 (d, J=245.8 Hz), 134.1 (d, J=6.2 Hz), 133.3, 132.7, 132.0, 130.1 (d, J=16.0 Hz), 129.9, 129.7, 128.6 (d, J=3.0 Hz), 124.9, 123.3 (d, J=9.9 Hz), 118.8 (d, J=24.3 Hz), 93.5 (d, J=3.1 Hz), 88.4, 59.6, 40.5, 34.0, 24.8 (d, J=2.5 Hz); ESI-HRMS calcd for $C_{19}H_{19}O_4S$ (M+H$^+$) 361.0467. found 361.0897.

Intermediate 5

1-Bromo-3-((methylsulfonyl)methyl)benzene

3-Bromobenzylbromide (260 mg, 1.04 mmol), sodium methanesulfinate (318 mg, 3.12 mmol) and DMF (2.5 mL) was added to a 10 mL cone shaped flask and stirred at 60° C. for 1 hour. The reaction was cooled to room temperature, added water and extracted with EtOAc (×3). The organic phases were combined, washed with water (×2), brine (×1), dried over MgSO$_4$ and concentrated under vacuum to give 252 mg (97%) of a white solid: $R_f$=0.15 (EtOAc:petroleum ether, 1:2); $^1$H NMR (CDCl$_3$) δ 7.60-7.52 (m, 2H), 7.37 (d, J=7.7 Hz, 1H), 7.30 (t, J=7.8 Hz, 1H), 4.21 (s, 2H), 2.80 (s, 3H); $^{13}$C NMR (CDCl$_3$) δ 133.4, 132.4, 130.6, 130.4, 129.2, 123.1, 60.6, 39.4; ESI-MS m/z 270.9 (M+Na$^+$).

Example 9

3-(2-Fluoro-4-((3-((methylsulfonyl)methyl)phenyl)ethynyl)phenyl)propanoic acid

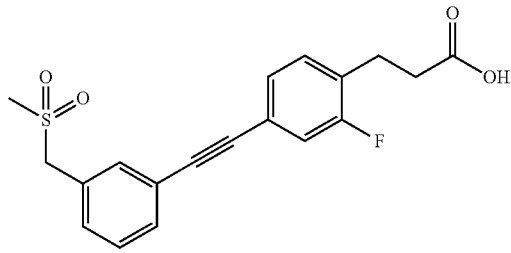 [SMILES: CS(=O)(=O)Cc1cccc(C#Cc2ccc(CCC(=O)O)c(F)c2)c1]

Methyl 3-(2-fluoro-4-((3-((methylsulfonyl)methyl)phenyl)ethynyl)phenyl)propanoate was prepared from methyl 3-(4-ethynyl-2-fluorophenyl)propanoate (102 mg, 0.50 mmol) and 1-bromo-3-((methylsulfonyl)methyl)benzene (138 mg, 0.55 mmol) according to the general procedure I to give 116 mg (62%) of a pale yellow solid after purification by flash chromatography (SiO$_2$, EtOAc:petroleum ether, 1:2): $R_f$=0.12 (EtOAc:petroleum ether, 1:2); $^1$H NMR (CDCl$_3$) δ 7.59-7.52 (m, 2H), 7.41 (d, J=4.9 Hz, 2H), 7.32-7.15 (m, 3H), 4.25 (s, 2H), 3.68 (s, 3H), 2.99 (t, J=7.7 Hz, 2H), 2.80 (s, 3H), 2.65 (t, J=7.7 Hz, 2H); $^{13}$C NMR (CDCl$_3$) δ 172.9, 160.6 (d, J=247.3 Hz), 133.5, 132.3, 130.7 (d, J=5.7 Hz), 130.5, 129.3, 128.7, 128.4 (d, J=16.0 Hz), 127.6 (d, J=3.3 Hz), 124.0, 122.7 (d, J=9.7 Hz), 118.3 (d, J=23.9 Hz), 89.2 (d, J=3.0 Hz), 88.8, 60.9, 51.7, 39.2, 33.9 (d, J=1.2 Hz), 24.6 (d, J=2.3 Hz); ESI-MS m/z 375.1 (M+H$^+$).

The title compound was prepared from methyl 3-(2-fluoro-4-((3-((methylsulfonyl)methyl)phenyl)ethynyl)phenyl)propanoate (90 mg, 0.24 mmol) according to the general procedure II to give 83 mg (96%) of a pale yellow solid (purity 99.7% by HPLC): $R_t$=10.56 min (HPLC); $^1$H NMR (Acetone-$d_6$) δ 7.68 (s, 1H), 7.62-7.45 (m, 3H), 7.40 (t, J=7.9 Hz, 1H), 7.31 (dd, J=16.8 Hz, 9.4 Hz, 2H), 4.47 (s, 2H), 2.98 (t, J=7.6 Hz, 2H), 2.90 (s, 3H), 2.66 (t, J=7.6 Hz, 2H); $^{13}$C NMR (Acetone-$d_6$) δ 173.5, 161.5 (d, J=245.9 Hz), 134.7, 132.4, 132.2, 132.0 (d, J=5.7 Hz), 131.1, 129.9 (d, J=16.0 Hz), 129.8, 128.5 (d, J=3.3 Hz), 124.0, 123.5 (d, J=9.9 Hz), 118.7 (d, J=24.2 Hz), 89.9, 89.2 (d, J=3.2 Hz), 60.4, 39.9, 34.0, 24.8 (d, J=2.5 Hz); ESI-HRMS calcd for $C_{19}H_{19}O_4S$ (M+H$^+$) 361.0467. found 361.0902.

Example 10

3-(2,6-Difluoro-4-(phenylethynyl)phenyl)propanoic acid

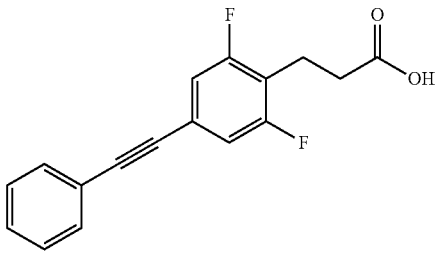

Ethyl (E)-3-(4-bromo-2,6-difluorophenyl)acrylate was prepared from 4-bromo-2,6-difluorobenzaldehyde (1006 mg, 4.55 mmol) and ethyl 2-bromoacetate (0.75 mL, 6.76 mmol) according to the general procedure III to give 1274 mg (96%) of a yellow solid after purification by flash chromatography (SiO$_2$, EtOAc:petroleum ether, 1:4): $R_f$=0.60 (EtOAc:petroleum ether, 1:2); $^1$H NMR (CDCl$_3$) δ 7.68 (d, J=16.5 Hz, 1H), 7.18-7.11 (m, 2H), 6.72 (d, J=16.5 Hz, 1H), 4.28 (q, J=7.1 Hz, 2H), 1.34 (t, J=7.1 Hz, 3H); $^{13}$C NMR (CDCl$_3$) δ 166.6, 161.3 (dd, J=260.1 Hz, 8.0 Hz), 129.7, 124.9 (dd, J=8.7 Hz, 8.7 Hz), 123.4 (dd, J=13.1 Hz, 13.1 Hz), 116.0 (dd, J=27.1 Hz, 2.7 Hz), 111.8 (dd, J=15.2 Hz, 15.2 Hz), 60.8, 14.3; ESI-MS m/z 291.0 (M+H$^+$).

Ethyl 3-(4-bromo-2,6-difluorophenyl)propanoate was prepared from (E)-ethyl 3-(4-bromo-2,6-difluorophenyl)acrylate (290 mg, 1.00 mmol) and NaBH$_4$ (102 mg, 2.70 mmol) at 0° C. according to the general procedure IV to give 202 mg (69%) of a clear oil after purification by flash chromatography (SiO$_2$, EtOAc:petroleum ether, 1:2): $R_t$=13.38 min (HPLC); $^1$H NMR (CDCl$_3$) δ 7.09-7.01 (m, 2H), 4.13 (q, J=7.1 Hz, 2H), 2.95 (t, J=7.8 Hz, 2H), 2.58 (t, J=7.8 Hz, 2H), 1.24 (t, J=7.1 Hz, 3H); $^{13}$C NMR (CDCl$_3$) δ 172.2, 161.3 (dd, J=251.5 Hz, 9.6 Hz), 127.9 (dd, J=10.1 Hz, 10.1 Hz), 119.7 (dd, J=12.1 Hz, 12.1 Hz), 115.2 (d, J=29.8 Hz), 61.6, 33.4, 17.9 (dd, J=2.5 Hz, 2.5 Hz), 14.1.

Ethyl 3-(2,6-difluoro-4-(phenylethynyl)phenyl)propanoate was prepared from ethyl 3-(4-bromo-2,6-difluorophenyl)propanoate (149 mg, 0.51 mmol) and phenylacetylene (0.07 mL, 0.64 mmol) according to the general procedure I to give 90 mg (56%) of a pale yellow solid after purification by flash chromatography (SiO$_2$, EtOAc:petroleum ether, 1:10): $R_f$=0.55 (EtOAc:petroleum ether, 1:2); $^1$H NMR (CDCl$_3$) δ 7.56-7.46 (m, 2H), 7.41-7.31 (m, 3H), 7.07-6.98 (m, 2H), 4.14 (q, J=7.1 Hz, 2H), 3.00 (t, J=7.8 Hz, 2H), 2.60 (t, J=7.8 Hz, 2H), 1.24 (t, J=7.1 Hz, 3H); $^{13}$C NMR (CDCl$_3$) δ 172.2, 161.1 (dd, J=248.4 Hz, 11.1 Hz), 131.7, 128.8, 128.4, 123.3 (dd, J=12.1 Hz, 12.1 Hz), 122.5, 116.9 (dd, J=20.2 Hz, 20.2

Hz), 114.4 (dd, J=19.9 Hz, 8.2 Hz), 90.9, 87.2 (dd, J=4.0 Hz, 4.0 Hz), 61.6, 33.6, 18.1, 14.2; ESI-MS m/z 337.1 (M+Na$^+$).

The title compound was prepared from ethyl 3-(2,6-difluoro-4-(phenylethynyl)phenyl)propanoate (78 mg, 0.25 mmol) according to the general procedure II to give 69 mg (97%) of a white solid (purity 99.6% by HPLC): R$_f$=12.71 min (HPLC); $^1$H NMR (Acetone-d$_6$) δ 7.62-7.52 (m, 2H), 7.49-7.38 (m, 3H), 7.22-7.12 (m, 2H), 3.00 (t, J=7.8 Hz, 2H), 2.63 (t, J=7.7 Hz, 2H); $^{13}$C NMR (Acetone-d$_6$) δ 173.2, 162.1 (dd, J=247.3 Hz, 10.1 Hz), 132.5, 129.9, 129.5, 124.1 (dd, J=12.6 Hz, 12.6 Hz), 123.3, 118.3 (dd, J=20.7 Hz, 20.7 Hz), 115.1 (dd, J=20.0 Hz, 8.5 Hz), 91.6, 87.7 (dd, J=3.7 Hz, 3.7 Hz), 33.5, 18.7 (dd, J=2.5 Hz, 2.5 Hz); ESI-HRMS calcd for C$_{17}$H$_{13}$F$_2$O$_2$ (M+H$^+$) 287.0878. found 287.0881.

Example 11

3-(3-Fluoro-4-(phenylethynyl)phenyl)propanoic acid

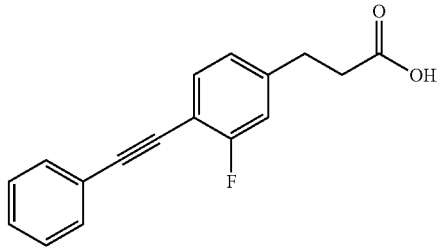 [SMILES: O=C(O)CCc1ccc(C#Cc2ccccc2)c(F)c1]

Ethyl (E)-3-(4-bromo-3-fluorophenyl)acrylate was prepared from 4-bromo-3-fluorobenzaldehyde (500 mg, 2.46 mmol) and ethyl 2-bromoacetate (0.40 mL, 3.61 mmol) according to the general procedure III to give 650 mg (97%) of a pale yellow oily product (purity ~90% by $^1$H NMR) after purification by flash chromatography (SiO$_2$, EtOAc:petroleum ether, 1:5): R$_f$=0.50 (EtOAc:petroleum ether, 1:2); $^1$H NMR (CDCl$_3$) δ 7.57 (dd, J=15.3 Hz, 5.3 Hz, 2H), 7.27 (d, J=9.3 Hz, 1H), 7.17 (d, J=8.3 Hz, 1H), 6.43 (d, J=16.0 Hz, 1H), 4.27 (q, J=7.1 Hz, 2H), 1.34 (t, J=7.1 Hz, 3H); $^{13}$C NMR (CDCl$_3$) δ 166.4, 159.3 (d, J=249.3 Hz), 142.1 (d, J=3.0 Hz), 135.9 (d, J=7.1 Hz), 134.0, 124.8 (d, J=4.0 Hz), 120.3, 115.2 (d, J=23.2 Hz), 111.0 (d, J=21.2 Hz), 60.8, 14.3; ESI-MS m/z 273.0 (M+H$^+$).

Ethyl 3-(4-bromo-3-fluorophenyl)propanoate was prepared from (E)-ethyl 3-(4-bromo-3-fluorophenyl)acrylate (310 mg, 1.14 mmol) and NaBH$_4$ (77 mg, 2.04 mmol) at 0° C. according to the general procedure IV to give 270 mg (87%) of a clear oily product: R$_f$=12.98 min (HPLC); $^1$H NMR (CDCl$_3$) δ 7.44 (t, J=7.7 Hz, 1H), 6.98 (d, J=9.5 Hz, 1H), 6.88 (d, J=8.2 Hz, 1H), 4.13 (q, J=7.1 Hz, 2H), 2.91 (t, J=7.5 Hz, 2H), 2.60 (t, J=7.5 Hz, 2H), 1.23 (t, J=7.1 Hz, 3H); $^{13}$C NMR (CDCl$_3$) δ 172.3, 159.0 (d, J=248.5 Hz), 142.4 (d, J=7.1 Hz), 133.4, 125.3 (d, J=4.0 Hz), 116.5 (d, J=22.2 Hz), 106.5 (d, J=21.2 Hz), 60.6, 35.3, 30.2 (d, J=1.2 Hz), 14.2.

Ethyl 3-(3-fluoro-4-(phenylethynyl)phenyl)propanoate was prepared from ethyl 3-(4-bromo-3-fluorophenyl)propanoate (137 mg, 0.50 mmol) and phenylacetylene (0.07 mL, 0.64 mmol) according to the general procedure I to give 115 mg (78%) of a brown oil after purification by flash chromatography (SiO$_2$, EtOAc:petroleum ether, 1:8): R$_f$=0.60 (EtOAc:petroleum ether, 1:2); $^1$H NMR (CDCl$_3$) δ 7.58-7.50 (m, 2H), 7.42 (t, J=7.7 Hz, 1H), 7.38-7.30 (m, 3H), 7.00-6.92 (m, 2H), 4.13 (q, J=7.1 Hz, 2H), 2.95 (t, J=7.6 Hz, 2H), 2.62 (t, J=7.6 Hz, 2H), 1.24 (t, J=7.1 Hz, 3H); $^{13}$C NMR (CDCl$_3$) δ 172.4, 162.6 (d, J=252.5 Hz), 143.5 (d, J=7.4 Hz), 133.3 (d, J=1.5 Hz), 131.7, 128.5, 128.4, 124.0 (d, J=3.2 Hz), 123.0, 115.5 (d, J=21.1 Hz), 109.7 (d, J=15.9 Hz), 94.0 (d, J=3.0 Hz), 82.7, 60.6, 35.3, 30.7 (d, J=1.2 Hz), 14.2; ESI-MS m/z 261.1 (M+H$^+$).

The title compound was prepared from ethyl 3-(3-fluoro-4-(phenylethynyl)phenyl)propanoate (102 mg, 0.35 mmol) according to the general procedure II to give 85 mg (92%) of a pale yellow solid (purity 99.6% by HPLC): R$_f$=12.24 min (HPLC); $^1$H NMR (Acetone-d$_6$) δ 7.61-7.47 (m, 3H), 7.47-7.39 (m, 3H), 7.22-7.13 (m, 2H), 2.98 (t, J=7.5 Hz, 2H), 2.68 (t, J=7.5 Hz, 2H); $^{13}$C NMR (Acetone-d$_6$) δ 173.6, 163.2 (d, J=250.7 Hz), 145.9 (d, J=7.6 Hz), 134.1, 132.2, 129.6, 129.5, 125.5 (d, J=3.0 Hz), 123.7, 116.4 (d, J=21.2 Hz), 110.0 (d, J=15.2 Hz), 94.5 (d, J=3.1 Hz), 83.3, 35.2, 31.2 (d, J=1.3 Hz); ESI-HRMS calcd for C$_{17}$H$_{14}$FO$_2$ (M+H$^+$) 269.0972. found 269.0978.

Intermediate 6

(Z)-3-Methylpent-2-en-4-yn-1-ol

To a mixture of water (30 mL) and 3-methylpent-1-en-4-yn-3-ol (5.0 g, 52 mmol) was added concentrated sulfuric acid (3.9 mL) and the reaction was stirred at room temperature for 2 days. The reaction was quenched with saturated NaHCO$_3$ solution and extracted with ether (3×). The organic layer was washed with brine, dried with Na$_2$SO$_4$ and concentrated in vacuo to yield a crude green liquid. The crude product was distilled at 70° C. for 1 h to remove excess of ether and starting material. The oil bath temperature was raised to 125° C. and vacuum was applied (10-15 mbar, vapour temperature—105° C.) which gave 2.81 g (56%) of a colorless oil (87% pure by HPLC with the E-isomer as major impurity): R$_t$=7.62 min; $^1$H NMR (CDCl$_3$) δ 5.96 (t, J=6.7 Hz, 1H), 4.34 (d, J=6.7 Hz, 2H), 3.18 (s, 1H), 1.91 (s, 3H); $^{13}$C NMR (CDCl$_3$) δ 137.4, 119.9, 82.2, 81.8, 61.3, 23.0.

Intermediate 7

(Z)-Ethyl 3-(2-fluoro-4-(5-hydroxy-3-methylpent-3-en-1-yn-1-yl)phenyl)propanoate A dried Schlenk flask charged with Na$_2$PdCl$_4$ (11 mg, 0.02 mmol), 2-(di-tert-butylphosphino)-N-phenylindole (PIntB, 25 mg, 0.04 mmol), CuI (7.0 mg, 0.02 mmol), ethyl 3-(4-bromo-2-fluorophenyl)propanoate (0.5 g, 1.82 mmol), TMEDA (3.3 mL) and water (0.36 mL), was evacuated and backfilled with argon three times, then heated to 75° C. (Z)-3-Methylpent-2-en-4-yn-1-ol (280 mg, 2.91 mmol) was added to the reaction mixture and then heated at 75° C. for 30 min. The reaction mixture was cooled to ambient temperature, diluted with water and extracted with ethyl acetate. The organic phases were combined, washed with brine, dried over Na$_2$SO$_4$ and concentrated in vacuo. The residue was purified by flash chromatography (SiO$_2$, EtOAc:petroleum ether, 3:7) to give 400 mg (75%) of a yellow oil (82% pure by HPLC with the E-isomer as major impurity): R$_t$=11.99 min; $^1$H NMR (CDCl$_3$) δ 7.20-7.12 (m, 2H), 7.09 (d, J=10.6 Hz, 1H), 5.94 (t, J=6.8 Hz, 1H), 4.40 (t, J=5.4 Hz, 2H), 4.12 (q, J=7.1 Hz, 2H), 2.97 (t, J=7.6 Hz, 2H), 2.62 (t, J=7.6 Hz, 2H), 1.97 (s, 3H), 1.50 (t, J=5.2 Hz, 1H), 1.23 (t, J=7.2 Hz, 3H); $^{13}$C NMR (CDCl$_3$) δ 172.6, 160.6 (d, J=246.2 Hz), 136.6, 130.7, 128.2, 128.1, 127.4, 123.0, 122.9, 120.0, 118.1 (d, J=23.7 Hz), 93.0, 88.0, 61.3, 60.6, 51.7, 34.2, 24.5, 23.0, 14.2.

Example 12

(Z)-3-(2-Fluoro-4-(5-hydroxy-3-methylpent-3-en-1-yn-1-yl)phenyl)propanoic acid

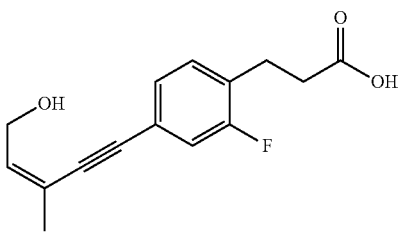 [SMILES: C/C(C#Cc1ccc(CCC(=O)O)c(F)c1)=C/CO]

The title compound was prepared from (Z)-ethyl 3-(2-fluoro-4-(5-hydroxy-3-methylpent-3-en-1-yn-1-yl)phenyl)propanoate (54 mg, 0.19 mmol) according to the general procedure II to give 23 mg (47%) of a white solid (purity 99.9% by HPLC) after purification with preparative HPLC: $R_f$=10.00 min; $^1$H NMR (CDCl$_3$) δ 7.21-7.13 (m, 2H), 7.10 (d, J=10.6 Hz, 1H), 5.95 (t, J=6.6 Hz, 1H), 4.40 (d, J=6.8 Hz, 2H), 2.98 (t, J=7.6 Hz, 2H), 2.69 (t, J=7.6 Hz, 2H), 1.97 (s, 3H); $^{13}$C NMR (CDCl$_3$) δ 177.1, 160.6 (d, J=246.5 Hz), 136.1, 130.6, 127.8 (d, J=15.9 Hz), 127.5, 123.06 (d, J=9.8 Hz), 120.7, 118.2 (d, J=23.7 Hz), 93.0, 87.9, 61.5, 33.6, 24.2, 23.1; ESI-HRMS calcd for C$_{15}$H$_{15}$FO$_3$Na (M+Na$^+$) 285.0897. found: 285.0896.

Example 13

3-(4-((3,5-Dichlorophenyl)ethynyl)-2-fluorophenyl)propanoic acid

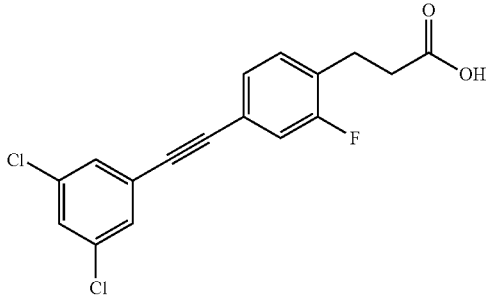 [SMILES: O=C(O)CCc1ccc(C#Cc2cc(Cl)cc(Cl)c2)cc1F]

Methyl 3-(4-((3,5-dichlorophenyl)ethynyl)-2-fluorophenyl)propanoate was prepared from methyl 3-(4-ethynyl-2-fluorophenyl)propanoate (103 mg, 0.50 mmol) and 1-bromo-3,5-dichlorobenzene (125 mg, 0.55 mmol) according to the general procedure I to give 128 mg (73%) of a pale yellow solid after purification by flash chromatography (SiO$_2$, EtOAc:petroleum ether, 1:5): $R_f$=0.49 (EtOAc:petroleum ether, 1:2); $^1$H NMR (CDCl$_3$) δ 7.39 (d, J=1.9 Hz, 2H), 7.33 (t, J=1.9 Hz, 1H), 7.24-7.20 (m, 2H), 7.19-7.14 (m, 1H), 3.68 (s, 3H), 2.99 (t, J=7.6 Hz, 2H), 2.65 (t, J=7.7 Hz, 2H); $^{13}$C NMR (CDCl$_3$) δ 172.9, 160.6 (d, J=247.5 Hz), 135.0, 130.8 (d, J=5.7 Hz), 129.8, 129.0, 128.8, 127.7 (d, J=3.3 Hz), 125.7, 122.1 (d, J=9.8 Hz), 118.4 (d, J=24.1 Hz), 90.4 (d, J=3.0 Hz), 87.1, 51.7, 33.9 (d, J=1.0 Hz), 24.6 (d, J=2.0 Hz).

The title compound was prepared from methyl 3-(4-((3,5-dichlorophenyl)ethynyl)-2-fluorophenyl)propanoate (100 mg, 0.29 mmol) according to the general procedure II to give 93 mg (96%) of a white solid (purity 99.9% by HPLC): $R_f$=14.38 min (HPLC); $^1$H NMR (DMSO-d$_6$) δ 12.25 (s, 1H), 7.73-7.68 (m, 1H), 7.67-7.60 (m, 2H), 7.45-7.30 (m, 3H), 2.88 (t, J=7.5 Hz, 2H), 2.57 (t, J=7.6 Hz, 2H); $^{13}$C NMR (DMSO-d$_6$) δ 173.3, 160.0 (d, J=245.4 Hz), 134.4, 131.1 (d, J=5.1 Hz), 129.8, 129.5 (d, J=16.0 Hz), 128.8, 127.8 (d, J=3.1 Hz), 125.2, 121.0 (d, J=9.8 Hz), 118.0 (d, J=24.3 Hz), 90.6, 86.9, 33.3, 23.6 (d, J=2.0 Hz); ESI-HRMS calcd for C$_{17}$H$_{11}$Cl$_2$FO$_2$Na (M+Na$^+$) 359.0012. found 359.0007.

Example 14

3-(4-((2-(Difluoromethyl)-5-fluorophenyl)ethynyl)-2-fluorophenyl)propanoic acid

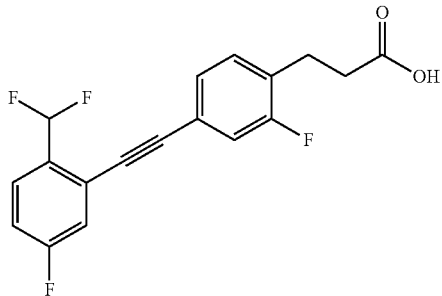 [SMILES: O=C(O)CCc1ccc(C#Cc2cc(F)ccc2C(F)F)cc1F]

Methyl 3-(4-((2-(difluoromethyl)-5-fluorophenyl)ethynyl)-2-fluorophenyl)propanoate was prepared from methyl 3-(4-ethynyl-2-fluorophenyl)propanoate (99 mg, 0.48 mmol) and 2-bromo-1-(difluoromethyl)-4-fluorobenzene (70 μL, 0.53 mmol) according to the general procedure I to give 118 mg (70%) of a pale yellow solid after purification by flash chromatography (SiO$_2$, EtOAc:petroleum ether, 1:5): $R_f$=0.47 (EtOAc:petroleum ether, 1:2); $^1$H NMR (CDCl$_3$) δ 7.66 (dd, J=8.7 Hz, 5.6 Hz, 1H), 7.30-7.15 (m, 5H), 7.02 (t, J=55.2 Hz, 1H), 3.68 (s, 3H), 3.00 (t, J=7.6 Hz, 2H), 2.65 (t, J=7.6 Hz, 2H); $^{13}$C NMR (CDCl$_3$) δ 172.8, 163.4 (dt, J=252.2 Hz, 1.9 Hz), 160.7 (d, J=247.9 Hz), 131.6 (dt, J=22.8 Hz, 3.3 Hz), 130.9 (d, J=5.7 Hz), 129.2 (d, J=16.1 Hz), 127.7 (d, J=3.3 Hz), 127.7 (dt, J=10.9 Hz, 5.7 Hz), 123.8 (dt, J=10.3 Hz, 6.1 Hz), 121.8 (d, J=9.7 Hz), 119.2 (d, J=23.6 Hz), 118.4 (d, J=24.1 Hz), 116.4 (d, J=22.0 Hz), 112.8 (t, J=238.8 Hz), 94.6 (d, J=3.1 Hz), 84.3-84.2 (m), 51.7, 33.9 (d, J=1.2 Hz), 24.6 (d, J=2.3 Hz); ESI-MS m/z 373.1 (M+Na$^+$).

The title compound was prepared from methyl 3-(4-((2-(difluoromethyl)-5-fluorophenyl)ethynyl)-2-fluorophenyl)propanoate (75 mg, 0.21 mmol) according to the general procedure II to give 68 mg (95%) of a white solid (purity 98.8% by HPLC): $t_R$=12.53 min (HPLC); $^1$H NMR (Acetone-d$_6$) δ 7.78 (dd, J=8.7 Hz, 5.6 Hz, 1H), 7.50-7.32 (m, 5H), 7.20 (t, J=54.9 Hz, 1H), 3.00 (t, J=7.6 Hz, 2H), 2.67 (t, J=7.6 Hz, 2H); $^{13}$C NMR (Acetone-d$_6$) δ 173.5, 164.4 (dt, J=250.5 Hz, 1.9 Hz), 161.5 (d, J=246.2 Hz), 132.7 (dt, J=22.7 Hz, 3.2 Hz), 132.1 (d, J=5.6 Hz), 130.8 (d, J=16.0 Hz), 128.9 (dt, J=9.7 Hz, 5.9 Hz), 128.7 (d, J=3.3 Hz), 124.6 (dt, J=10.4 Hz, 5.9 Hz), 122.6 (d, J=9.8 Hz), 120.0 (d, J=24.0 Hz), 119.0 (d, J=24.4 Hz), 117.4 (d, J=22.3 Hz), 114.1 (t, J=237.0 Hz), 95.3 (d, J=3.1 Hz), 94.9 (d, J=2.8 Hz), 34.0 (d, J=0.9 Hz), 24.8 (d, J=2.6 Hz); ESI-HRMS calcd for $C_{18}H_{12}F_4O_2Na$ (M+Na$^+$) 359.0666. found 359.0680.

Biological Assays

The compounds were tested for their ability to mobilize calcium in GPR40-transfed cells as described by Christiansen et al. (J. Med. Chem. 2011, 54, 6691-6703). Results for selected examples are given in Table 1.

TABLE 1

| Example | GPR40 activity (pEC$_{50}$) |
|---|---|
| 1 | 7.48 |
| 2 | 7.09 |
| 3 | 7.69 |
| 4 | 7.43 |
| 5 | 7.48 |
| 6 | 8.21 |
| 7 | 7.77 |
| 8 | 5.84 |
| 9 | 5.71 |
| 10 | 6.85 |
| 11 | 6.84 |
| 12 | 6.37 |
| 13 | 7.42 |
| 14 | 7.74 |

Glucose Tolerance Test in Normal Mice

The study was conducted in accordance with UK Government Home Office regulations, C57Bl/6 mice (6-7 weeks, Charles River) were given chow diet (Bantin and Kingman, no 1 diet) and water ad lib. The mice were under controlled lighting conditions (lights on 8.00 h, 12 h light/12 h dark) and at a room temperature of 21°±1° C. The study was performed after a few days rest to adapt to new environment and caging. Mice were randomised to achieve similar mean body weight in each cage. 36 male C57Bl/6 mice were grouped as follows:

| A | 2 groups of 3 mice | control |
|---|---|---|
| B | 2 groups of 3 mice | TUG 770 - 2 mg/kg p.o. |
| C | 2 groups of 3 mice | TUG 770 - 10 mg/kg p.o. |
| D | 2 groups of 3 mice | TUG 770 - 50 mg/kg p.o. |
| E | 2 groups of 3 mice | TUG 770 - 250 mg/kg p.o. |
| F | 2 groups of 3 mice | sitagliptin 10 mg/kg p.o. |

Five hours prior to the start of the glucose tolerance test (07.00) food was removed and animals were given clean cages. Mice were treated with vehicle (10% (v/v) Cremophor, 10% DMSO, 80% of 5% mannitol in water) or compound at 11.30 h and glucose at 12.00 h. Glucose was dissolved in water (2 g/10 ml) and given to the mice i.p. with a load of 2 g/kg. Blood samples (20M were taken for the analysis of glucose concentrations at −30, 0, 20, 40, 60, 90 and 120 minutes following glucose administration.

Blood Glucose Analysis

20 µl samples of blood were taken into disposable micropipettes (Dade Diagnostics Inc., Aguada, Puerto Rico) and glucose concentrations determined after mixing with 0.38 ml of haemolysis reagent. Duplicate 20 µl aliquots of this mixture was taken for each individual sample and placed in a 96-well assay plate. To each well was added 180 µl aliquots of glucose oxidase reagent (Thermo Trace, Victoria, Australia. Cat no TR5221), the samples were mixed and then left for approximately 30 minutes. Samples were then analysed automatically using a SpectraMax-250 and SoftMax Pro software (Molecular Devices Corporation, 1311 Orleans Drive, Sunnyvale, Calif. 94089, USA). The results were converted into glucose concentration values using Prism software, version 3.0 (GraphPad Software Inc., San Diego, Calif., USA).

Figure 2:
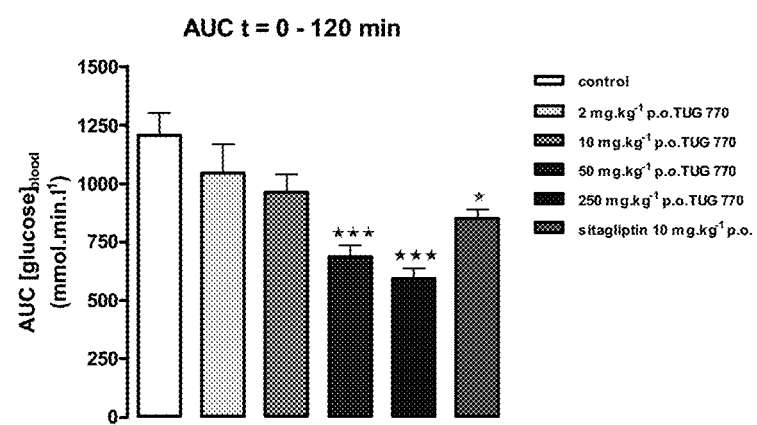

The plasma glucose concentrations of vehicle control, compound TUG-770 (Example 6) in oral doses of 2, 10, 50 and 250 mg/kg and sitagliptin (10 mg/kg p.o.) has been plotted against time in FIG. 1. The areas under the curve (AUC) for each group are shown in FIG. 2.

The invention claimed is:

1. A compound of the formula (I)

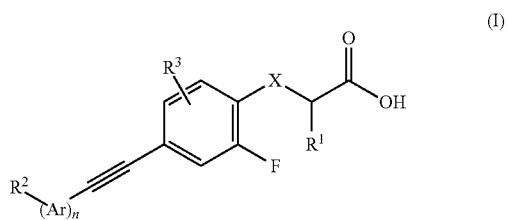

or a salt thereof
wherein
Ar is an optionally substituted monocyclic or fused aromatic or heteroaromatic ring system;
n is an integer of 0-1;
X is —C(R$^4$R$^5$);
m is an integer of 0-2;
R$^1$, R$^4$, and R$^6$ are independently selected from the group consisting of hydrogen, optionally substituted (C$_1$-C$_{10}$)alkyl, optionally substituted (C$_2$-C$_{10}$)alkenyl, optionally substituted (C$_2$-C$_{10}$)alkynyl, optionally substituted (C$_1$-C$_{10}$)alkylene, optionally substituted (C$_1$-C$_{10}$)alkoxy, hydroxy, optionally substituted (C$_2$-C$_{10}$)dialkylamino, optionally substituted (C$_1$-C$_{10}$)alkylthio, optionally substituted (C$_2$-C$_{10}$)heteroalkyl, optionally substituted (C$_2$-C$_{10}$)heteroalkylene, optionally substituted (C$_3$-C$_{10}$)cycloalkyl, optionally substituted (C$_3$-C$_{10}$)heterocycloalkyl, optionally substituted (C$_3$-C$_{10}$)cycloalkylene, optionally substituted (C$_3$-C$_{10}$)heterocycloalkylene, halo, nitrile, (C$_1$-C$_{10}$)alkylsulfenyl, (C$_1$-C$_{10}$)alkylsulfinyl, optionally substituted (C$_1$-C$_{10}$)alkylsulfonyl, optionally substituted (C$_1$-C$_{10}$)haloalkyl, optionally substituted (C$_1$-C$_{10}$)perhaloalkyl, (C$_2$-C$_{10}$)-alkenyloxy, (C$_3$-C$_{10}$)-alkynyloxy, aryloxy, arylalkyloxy, heteroaryloxy, heteroarylalkyloxy, (C$_1$-C$_6$)alkyloxy-(C$_1$-C$_4$)alkyl optionally substituted aryl, optionally substituted heteroaryl, and optionally substituted arylalkyl;
R$^2$ is selected from the group consisting of hydrogen, optionally substituted (C$_1$-C$_{10}$)alkyl, optionally substituted (C$_2$-C$_{10}$)alkenyl, optionally substituted (C$_2$-C$_{10}$)alkynyl, optionally substituted (C$_1$-C$_{10}$)alkylene, optionally substituted (C$_2$-C$_{10}$)heteroalkyl, optionally substituted (C$_2$-C$_{10}$)heteroalkenyl, optionally substituted (C$_2$-C$_{10}$)heteroalkylene, optionally substituted (C$_3$-C$_{10}$)cycloalkyl, optionally substituted (C$_3$-C$_{10}$)cycloalkenyl, optionally substituted (C$_3$-C$_{10}$)cycloalkylene, optionally substituted (C$_3$-C$_{10}$)heterocycloalkyl, optionally substituted (C$_3$-C$_{10}$)heterocycloalkenyl, optionally substituted (C$_3$-C$_{10}$)heterocycloalkylene, optionally substituted (C$_1$-C$_{10}$)haloalkyl, optionally substituted (C$_1$-C$_{10}$)haloalkenyl, optionally substituted (C$_1$-C$_{10}$)haloalkylene, optionally substituted (C$_1$-C$_{10}$)perhaloalkyl, optionally substituted (C$_1$-C$_{10}$)perhaloalkenyl, optionally substituted $(C_1-C_{10})$perhaloalkylene, and optionally substituted arylalkyl;

Ar and $R^2$ may be further substituted by $R^6$;

$R^3$ is selected from hydrogen and halogen;

$R^5$ is selected from hydrogen and optionally substituted $(C_1-C_3)$alkyl;

wherein substituted means one or more substituents selected from: —OR', =O, =NR', =N—OR', —NR'R", —SR', halogen, —OC(O)R', —C(O)R', —CO$_2$R', —CONR'R", —OC(O)NR'R", —NR'—C(O)NR"R''', —NR'—SO$_2$NR"R''', —NH—C(NH$_2$)=NH, —NR'C(NH$_2$)=NH, —NH—C(NH$_2$)=NR', —SiR'R"R''', —S(O)R', —SO$_2$R', —SO$_2$NR'R", —NR"SO$_2$R, —CN, —(C$_2$-C$_5$)alkynyl, —(C$_2$-C$_5$)alkenyl, and —NO$_2$, said R', R" and R''' each independently refer to hydrogen, unsubstituted (C$_1$-C$_6$)alkyl and (C$_2$-C$_6$)heteroalkyl, unsubstituted aryl, aryl substituted with one to three halogens, unsubstituted (C$_1$-C$_4$)-alkyl, (C$_1$-C$_4$)-alkoxy or (C$_1$-C$_4$)-thioalkoxy groups, halo(C$_1$-C$_4$)alkyl, or aryl-(C$_1$-C$_4$)alkyl groups, provided that when R' and R" are attached to the same nitrogen atom, they can be combined with the nitrogen atom to form a 5-, 6- or 7-membered ring;

with the proviso that the following compound is excluded from protection:

(S)-2-tert-butoxycarbonylamino-3-(4-{(R)-4-[1-(5-chloropyrimidin-2-yl)-piperidin-4-yl]pent-1-ynyl}-2-fluorophenyl)propionic acid.

2. The compound of claim 1 or a salt thereof, wherein $R^1$, $R^4$ and $R^6$ are independently selected from hydrogen and $(C_1-C_3)$alkyl.

3. The compound of claim 1 or a salt thereof, wherein $R^1$ is hydrogen.

4. The compound of claim 1 or a salt thereof, wherein $R^4$ and $R^5$ are hydrogen.

5. The compound of claim 1 or a salt thereof, wherein $R^3$ is hydrogen.

6. The compound of claim 1 or a salt thereof, wherein n is 1 and Ar is selected from the group consisting of an optionally substituted phenyl, 2-pyridyl, 3-pyridyl, 4-pyridyl, 2-thienyl, 3-thienyl, 2-thiazolyl, 4-thiazolyl, 5-thiazolyl, 4-thiazolyl, 2-furyl, 3-furyl, 2-oxazolyl, 4-oxazolyl, 5-oxazolyl, 2-pyrrolyl, 3-pyrrolyl, 1-pyrrazolyl, 2-pyrrazolyl, 3-pyrrazolyl, 2-pyrimidyl, 4-pyrimidyl, 5-pyrimidyl, 4-triazolyl, 5-tetrazolyl, 2-naphthyl, 3-naphthyl, 2-quinolyl, 3-quinolyl, 4-quinolyl, 5-quinolyl, 6-quinolyl, 7-quinolyl, 8-quinolyl, 2-benzothiazolyl, 4-benzothiazolyl, 5-benzothiazolyl, 6-benzothiazolyl, 7-benzothiazolyl, 1-indolyl, 2-indolyl, 3-indolyl, 4-indolyl, 5-indolyl, 6-indolyl and 7-indolyl.

7. The compound of claim 1 or a salt thereof, wherein n is 1 and Ar is phenyl.

8. The compound of claim 1 or a salt thereof, wherein n is 1 and Ar is 4-pyridyl.

9. The compound of claim 7 or a salt thereof, with $R^2$ substituted in the ortho or meta position relative to the alkyne of formula (I).

10. The compound of claim 9 or a salt thereof, wherein $R^2$ is selected from hydrogen and $(C_1-C_6)$alkyl.

11. The compound of claim 1 or a salt thereof, wherein $R^1$ is methyl, $R^4$ and $R^5$ are hydrogen, and $R^1$ is connected to X with a covalent bond.

12. The compound of claim 1 or a salt thereof, wherein n is 0 and $R^2$ is selected from $(C_1-C_{10})$alkyl, $(C_2-C_{10})$alkenyl, $(C_2-C_{10})$heteroalkyl, $(C_2-C_{10})$heteroalkenyl, $(C_3-C_{10})$cycloalkyl, $(C_3-C_{10})$cycloalkenyl, $(C_5-C_{10})$bicycloalkyl, $(C_5-C_{10})$heterobicycloalkyl and $(C_3-C_{10})$heterocycloalkenyl.

13. The compound of claim 12 or a salt thereof, wherein $R^2$ is selected from $(C_1-C_6)$alkyl, $(C_2-C_6)$alkenyl, $(C_2-C_6)$heteroalkyl, $(C_2-C_6)$heteroalkenyl, $(C_3-C_6)$cycloalkyl and $(C_3-C_6)$cycloalkenyl.

14. The compound of claim 12 or a salt thereof, wherein $R^2$ is vinyl substituted by 1-3 $(C_1-C_3)$alkyls.

15. The compound of claim 1 or a salt thereof, wherein n is 0 and $R^2$ is $(C_4-C_6)$cycloalken-1-yl substituted by 1-3 $R^6$ groups.

16. A process for the preparation of a compound of claim 1 or a salt thereof, comprising any combination of three or more steps from the alternative pathways:

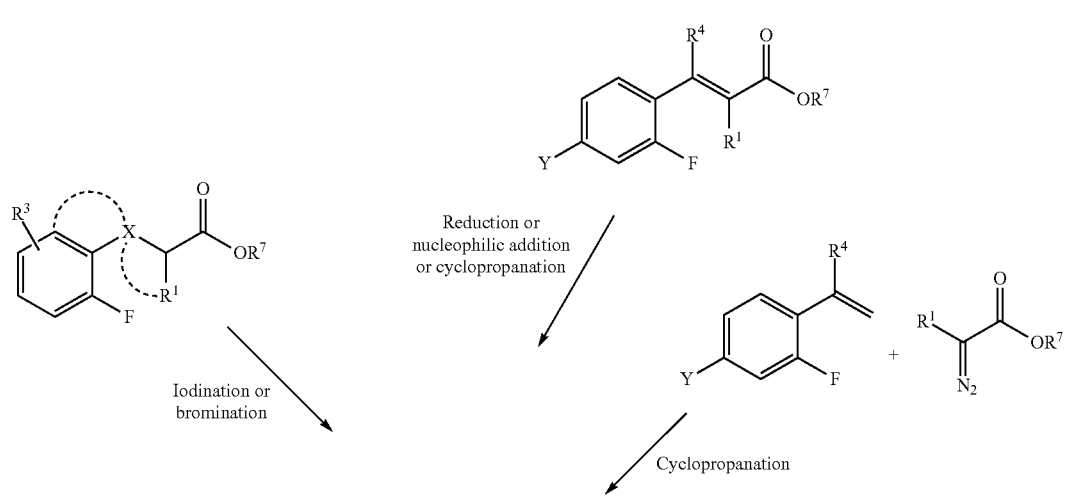

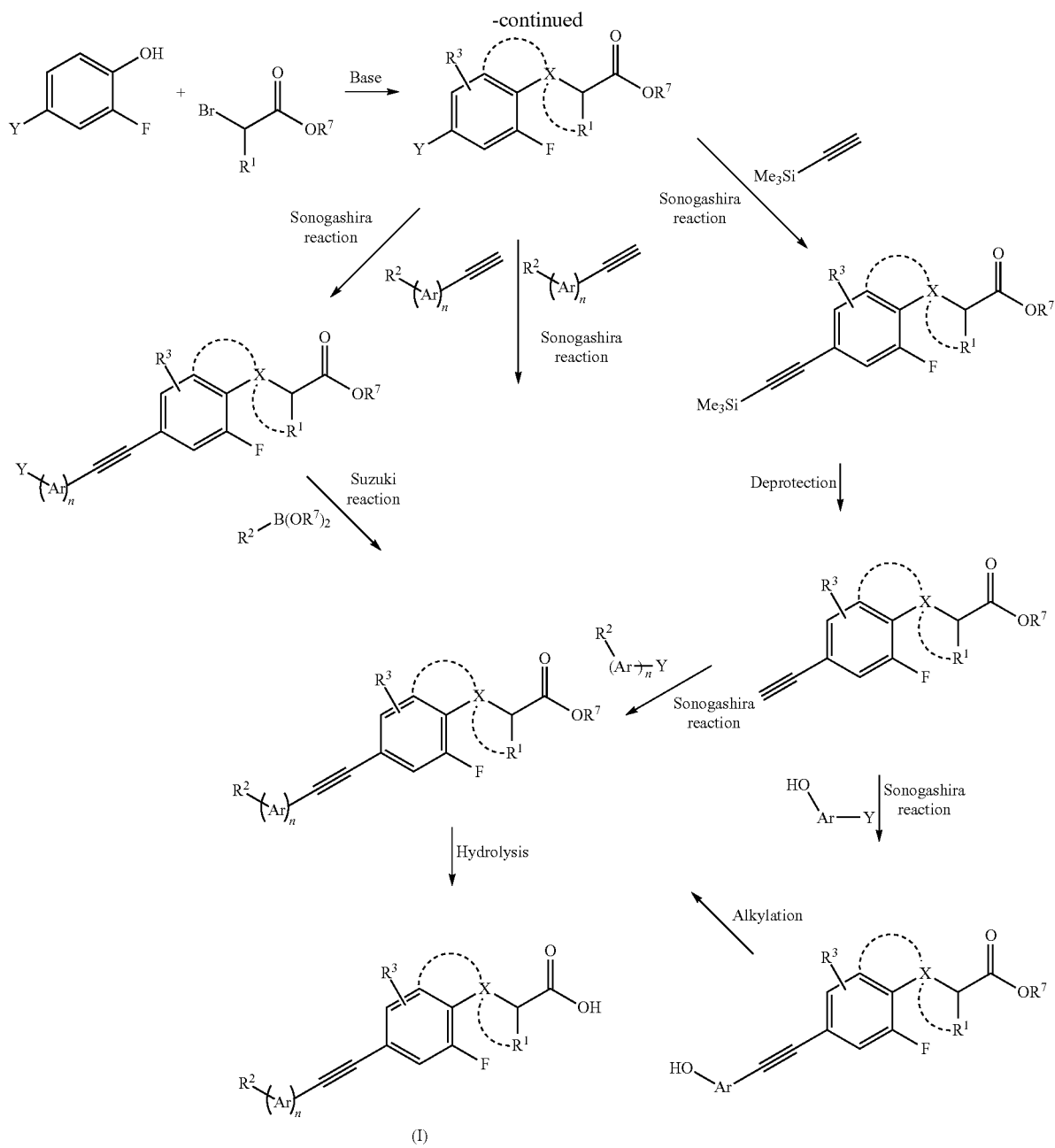
wherein R7 is selected from hydrogen and $(C_1\text{-}C_{10})$alkyl, and Y is selected from halogen and triflate.
* * * * *